US012624099B2

(12) United States Patent
Lee et al.

(10) Patent No.: US 12,624,099 B2
(45) Date of Patent: May 12, 2026

(54) POLYPEPTIDE IMPROVED IN PROTEIN PURITY AND AFFINITY FOR ANTIGEN, CONJUGATE THEREOF WITH ANTIBODY OR ANTIGEN-BINDING FRAGMENT, AND PREPARATION METHOD THEREFOR

(71) Applicant: ABCLON INC., Seoul (KR)

(72) Inventors: Jong Ho Lee, Gyeonggi-do (KR); Hyun Jong Lee, Incheon (KR); Bong Kook Ko, Seoul (KR); Kyu Tae Kim, Gyeonggi-do (KR); Jong Seo Lee, Gyeonggi-do (KR)

(73) Assignee: ABCLON INC., Seoul (KR)

( * ) Notice: Subject to any disclaimer, the term of this patent is extended or adjusted under 35 U.S.C. 154(b) by 1424 days.

(21) Appl. No.: 16/606,402

(22) PCT Filed: Apr. 18, 2018

(86) PCT No.: PCT/KR2018/004516
§ 371 (c)(1),
(2) Date: Oct. 18, 2019

(87) PCT Pub. No.: WO2018/194376
PCT Pub. Date: Oct. 25, 2018

(65) Prior Publication Data
US 2021/0122816 A1 Apr. 29, 2021

(30) Foreign Application Priority Data
Apr. 18, 2017 (KR) ........................ 10-2017-0049732

(51) Int. Cl.
*C07K 16/24* (2006.01)
*A61K 39/00* (2006.01)

(52) U.S. Cl.
CPC ............ *C07K 16/248* (2013.01); *A61K 39/00* (2013.01); *C07K 16/241* (2013.01); *C07K 2317/31* (2013.01); *C07K 2317/41* (2013.01); *C07K 2318/20* (2013.01); *C07K 2319/00* (2013.01)

(58) Field of Classification Search
None
See application file for complete search history.

(56) References Cited

U.S. PATENT DOCUMENTS

| | | |
|---|---|---|
| 2009/0175872 A1 | 7/2009 | Mi et al. |
| 2010/0291112 A1 | 11/2010 | Kellner et al. |

FOREIGN PATENT DOCUMENTS

| | | |
|---|---|---|
| JP | H9508016 A | 8/1997 |
| JP | 2011-509073 A | 3/2011 |
| KR | 2017-0018888 A | 2/2017 |
| WO | WO-95/19374 A1 | 7/1995 |
| WO | WO-2009/080811 A1 | 7/2009 |
| WO | WO-2015/189430 A1 | 12/2015 |
| WO | WO-2015/189431 A1 | 12/2015 |

OTHER PUBLICATIONS

Sailer et al. 'Molecular ensembles make evolution unpreictable.' PNAS 114(45):11938-11943, 2017.*
Office Action from corresponding Chinese Patent Application No. 201880026193.4, dated Oct. 27, 2022.
Lindborg, M., et al.; "High-affinity binding to staphylococcal protein A by an engineered dimeric Affibody molecule", Protein Engineering, Design & Selection vol. 26 No. 10 pp. 635-644, 2013.
Extended European Search Report from corresponding European Patent Application No. 18787034.0, dated Aug. 24, 2020.
Yu, F., et al.; "Supplementary Material to an Affibody-Adalimumab Hybrid Blocks Combined IL-6 and TNF-Triggered Serum Amyloid a Secretion In Vivo" mAbs, Dec. 15, 2014, pp. 1-11.
Yu, F., et al.; "Generating Affinity Proteins for Biotechnological, Diagnostic and Therapeutic Applications" Thesis paper, Jan. 1, 2015, 111 pages.
Vazquez-Lombardi, R., et al.; "Challenges and Opportunities for Non-Antibody Scaffold Drugs", Drug Discovery Today, vol. 20, No. 10, Oct. 1, 2015, pp. 1271-1283.
Frejd, F. Y., et al.: "Affibody Molecules as Engineered Protein Drugs", Experimental & Molecular Medicine, vol. 49, No. 3, Mar. 1, 2017, pp. 1-8.
Yamaguchi, K., et al.; "Effects of Site-Directed Removal of N-Glycosylation Sites in Human Erythropoietin on Its Production and Biological Properties", Journal Of Biological Chemistry, American Society For Biochemistry And Molecular Biology, vol. 266, No. 30, Oct. 25, 1991, pp. 20434-20439.
International Search Report from corresponding PCT Application No. PCT/KR2018/004516, mailed on Sep. 10, 2018.
Lindborg, Malin et al., "High-affinity Binding to Staphylococcal Protein A by an Engineered Dimeric Affinbody Molecule", Protein Engineering, Design & Selection, 2013, vol. 26, No. 10, pp. 635-644.
Lendel, Christofer et al., "Structural Basis for Molecular Recognition in an Affibody; Affibody Complex", Journal of Molecular Biology, 2006, vol. 359, No. 5, pp. 1293-1304.
Tashiro, Mitsuru et al., "Structures of Bacterial Immunoglobulin-binding Domains and Their Complexes with Immunoglobulins", Current Opinion in Structural Biology, 1995, vol. 5, No. 4, pp. 471-481.

(Continued)

*Primary Examiner* — Nora M Rooney
(74) *Attorney, Agent, or Firm* — Harness, Dickey & Pierce, P.L.C.

(57) ABSTRACT
The present invention relates to a polypeptide improved in protein purity and in affinity for a target antigen, a conjugate thereof with an antibody or antigen-binding fragment, and a preparation method of the polypeptide and the conjugate. The polypeptide or the conjugate thereof according to the present invention does not undergo glycosylation even when produced in a eukaryotic cell and thus has high protein purity and affinity for a target antigen, showing a very high value as a reagent for diagnosis or treatment of a disease.

10 Claims, 8 Drawing Sheets

Specification includes a Sequence Listing.

(56) References Cited

OTHER PUBLICATIONS

Yu, Feifan et al., "An Affibody-adalimumab Hybrid Blocks Combined IL-6 and TNF-triggered Serum Amyloid A Secretion in Vivo", mAbs, 2014, vol. 6, No. 6, pp. 1598-1607.

Orlova, A., et al., "Tumor Imaging Using a Picomolar Affinity HER2 Binding Affibody Molecule", Cancer Res 2006; 66: (8), pp. 4339-4349.

Goldstein, R., et al.; "Developments in single photon emission computed tomography and PET-based HER2 molecular imaging for breast cancer", Expert Rev. Anticancer Ther. 13(3), 359-373 (2013).

Wright, A., et al.; "Antibody variable region glycosylation: position effects on antigen binding and carbohydrate structure", The EMBO Journal vol. 10 No. 10 pp. 2717-2723, 1991.

Grönwall, C., et al.: "Selection and characterization of Affibody ligands binding to Alzheimer amyloid β peptides", Journal of Biotechnology 128 (2007) 162-183.

Office Action from corresponding Japanese Patent Application No. 2019-557471, dated Dec. 1, 2020.

* cited by examiner

Lane M : Standard Marker
Lane 1 : NL5 Parent        2ug
Lane 2 : NL5 SM1           2ug
Lane 3 : NL5 SM2           2ug
Lane 4 : NL5 DM1           2ug Lane M : Standard Marker
Lane 1 : CL5 Parent     2ug
Lane 2 : CL5 SM1     2ug
Lane 3 : CL5 SM2     2ug
Lane 4 : CL5 DM1     2ug Lane M : Standard Marker Lane 1 : NH5 Parent          2ug Lane 2 : NH5 SM1          2ug Lane 3 : NH5 SM2          2ug Lane 4 : NH5 DM1          2ug

EC50

| | NLS-W | NLS-SM1 | NLS-SM2 | NLS-DM1 |
|---|---|---|---|---|
| Double | 2.162 | 2.601 | 0.5384 | 0.5125 |
| IL-6 | 0.6374 | 0.6901 | 0.2604 | 0.3138 |
| TNF-a | 0.5283 | 0.422 | 0.3061 | 0.3229 |

| | CLS-W | CLS-SM1 | CLS-SM2 | CLS-DM1 |
|---|---|---|---|---|
| Double | 0.4302 | 0.5958 | 0.3299 | 0.2961 |
| IL-6 | 1.162 | 1.307 | 0.5821 | 0.4706 |
| TNF-a | 0.1661 | 0.1663 | 0.1665 | 0.1881 |

FIG. 7B

POLYPEPTIDE IMPROVED IN PROTEIN PURITY AND AFFINITY FOR ANTIGEN, CONJUGATE THEREOF WITH ANTIBODY OR ANTIGEN-BINDING FRAGMENT, AND PREPARATION METHOD THEREFOR

CROSS-REFERENCE TO RELATED APPLICATIONS

This application is a national phase application of PCT Application No. PCT/KR2018/004516, filed on Apr. 18, 2018, which claims benefit of Korean Patent Application 10-2017-0049732, filed on Apr. 18, 2017. The entire disclosure of the applications identified in this paragraph are incorporated herein by references.

FIELD

The present invention relates to a polypeptide improved in protein purity and affinity for an antigen, a complex of the polypeptide with an antibody or an antigen-binding fragment thereof, a method for producing the polypeptide, and a method for producing the complex. More specifically, the present invention relates to a polypeptide and the like, which are improved in protein purity and affinity for an antigen by substituting an amino acid residue at a specific position in the scaffold of a known polypeptide to thereby prevent glycosylation when the polypeptide and the like are expressed in eukaryotic cells.

BACKGROUND

Affibody® molecules are small proteins composed of 58 amino acid residues based on the Z domain, which is an affinity site for IgG in Protein A from *Staphylococcus aureus*. In protein sequencing of the Affibody molecules, 13 amino acids that form the binding surface with IgG can bind to various target antigens depending on the amino acid sequence thereof and can be randomly arranged to construct libraries. Similar to antibodies, Affibody molecules capable of binding to various target antigens can be screened from libraries through screening methods, such as phage display and yeast two hybrid (Y2H). Affibody molecules specifically binding to HER2 and amyloid-β have been recently developed using characteristics of Affibody molecules capable of binding to target antigens (Orlova et al. 2006, Cancer Res., and Gronwall et al., 2007, J. Biotechnol). Since the Affibody molecules have a very small molecular weight of 6 kDa, the Affibody molecules are systemically diffused and fast removed through kidney filtration when administered into the human body. Therefore, Affibody molecules are mainly applied to the research and development of diagnostic species (Goldstein R et al., 2013, Expert Rev Anticancer Ther). Affibody molecules have also been developed in the form of double antibodies binding to general IgG (Yu F et al., 2014, MAbs).

Protein post-translation modification (PTM) occurs in cells of eukaryotic creatures including humans. Examples of post-translational modification are acetylation, phosphorylation, and the like, and such a post-translational modification affects protein diversity, plays an important role in intracellular signaling, and regulates cellular physiology. Such an abnormal post-translational modification occurring in intercellular proteins causes a variety of diseases including cancer. However, the sequence information of a particular protein alone makes it impossible to accurately predict whether the protein will undergo post-translational modification. Therefore, protein identification needs to be accompanied by a task of checking, through a variety of experiments, whether or not post-translational modification occurs.

In cases where a protein to be expressed is expressed in eukaryotes, such as animal cells, but not prokaryotes, such as bacteria, there is a possibility of producing proteins having no desired characteristics by such post-translational modification. For example, it has been reported that the occurrence of glycosylation, which is a kind of post-translational modification, in an antibody variable region, may drop the homogeneity of antibodies and disturb target-specific binding thereof (Wright A et al., 1991, EMBO).

PCT Publication WO95/19374 discloses first-generation Z variant-based polypeptide scaffolds and PCT Publication WO2009/080811 discloses second-generation Z variant-based polypeptide scaffolds.

However, the cited documents do not disclose, teach, and suggest the occurrence or not of post-translational modification (i.e., glycosylation) as in the present invention and the effect of the post-translational modification on homogeneity or target-specific binding ability of polypeptides as a resultant product, and do not recognize the need of improvement thereof.

Above all, there is a continuous need for improvement of protein purity (homogeneity) and target-specific binding ability in cases of medicinal products using polypeptides, especially, polypeptides using target-specific binding characteristics.

Throughout the present specification, many papers and patent documents are used as references, and the citations thereof are represented. The disclosure of the cited papers and patent documents is incorporated in the present specification by reference in its entirety to describe the level of the technical field to which the present invention pertains and the content of the present invention more clearly.

SUMMARY

Technical Problem

The present inventors found that in cases where Affibody® molecules, which are a kind of Z variant-based polypeptide scaffold, are expressed in eukaryotic cells, the binding characteristics thereof may be degraded due to the presence of a post-translational modification site in a sequence associated with target binding. The present inventors confirmed from such a fact that as a result of producing Affibody proteins with antigen-specific binding ability in animal cells, glycosylation actually occurred at a target binding site to badly affect protein homogeneity and target-specific binding.

Therefore, the present inventors endeavored to develop an Affibody molecule having an amino acid sequence, which has no possibility of degrading protein homogeneity and target-specific binding characteristics even when expressed in eukaryotes. As a result, the present inventors confirmed that the Affibody molecules with amino acid modifications (substitutions) at two positions in the full-length amino acid sequence of 58 amino acids caused no glycosylation and had enhanced binding ability to an antigen (especially, IL-6).

Therefore, an aspect of the present invention is to provide a polypeptide (Affibody molecule) improved in protein purity and affinity for a target antigen through glycosylation prevention even when produced in eukaryotic cells.

Another aspect of the present invention is to provide a polypeptide complex, which contains the polypeptide (Affibody molecule) and an antibody or an antigen-binding fragment thereof specifically binding to any target antigen and thus is improved in protein purity and affinity for a target antigen.

Still another aspect of the present invention is to provide a method for producing the polypeptide (Affibody molecule) and a method for producing the polypeptide complex containing the polypeptide and the antibody or the antigen-binding fragment thereof.

Other purposes and advantages of the present disclosure will become more obvious when taken with the following detailed description of the invention, claims, and drawings.

Technical Solution

As used herein, the term "affinity" refers to a property or ability to specifically bind to a specific target. The term is used to indicate the intensity of binding strength between specific substances, for example, the binding ability between an enzyme and a substrate or the binding ability between an antibody and an antigen, in the field of biology as in the present invention.

As used herein, the term "amino acid" refers to a most basic constituent unit of protein molecules. In the structure of amino acids, an amino group ($—NH_2$) and a carboxyl group ($—COOH$) are attached to one carbon atom, to which hydrogen and an R group are linked.

As used herein, the term "protein" refers to a polymeric organic material constituting a body of all the animals, and the protein is a connected body of numerous amino acids. There are about 20 kinds of natural amino acids, and a long, unbranched chain of amino acids linked to each other via chemical bonds called peptide bonds is referred to as a polypeptide. The polypeptide of the present invention may be prepared by a synthesis method known in the art, for example, an expression vector containing a protein-expressing nucleic acid is transformed into host cells to synthesize a recombinant protein, or the polypeptide may be prepared by solid-phase synthesis techniques (Merrifield, J. Amer. Chem. Soc. 85:2149-54 (1963); and Stewart, et al., Solid Phase Peptide Synthesis, 2nd. ed., Pierce Chem. Co.: Rockford, 111 (1984)).

As used herein, the term "glycosylation" is a kind of post-translational modification in cells (eukaryotes), and the glycosylation reaction occurs in the Golgi body. The glycosylation is divided into N-glycosylation and O-glycosylation, which are different with respect to the attached functional group. The processes in which a sugar, such as lactose or fucose, is attached to a protein produced in cells are collectively called "glycosylation". In the glycosylation processes, glycans are linked to a protein, and the protein undergoes "folding" to from a three-dimensional structure. Such a structure imparts stability to the protein that the protein can remain without disintegration for a long period of time. In addition, the glycans attached to the protein migrate into cell membranes to become a cell membrane protein, which often exerts the same effects as an antigen. Such a glycosylated protein is called glycoprotein, and a representative glycoprotein is an antibody that plays an important role in an immune response.

In accordance with an aspect of the present invention, there is provided a polypeptide including an amino acid sequence of General Formula 1 below, wherein:

i) T is substituted with N at the 23rd amino acid position in General Formula 1 below, ii) S is substituted with A at the 54th amino acid position in General Formula 1 below, and iii) T and S are substituted with N and A at the 23rd and 54th amino acid positions in General Formula 1, respectively, whereby glycosylation is prevented upon the production of the polypeptide in eukaryotic cells and thus the polypeptide is improved in protein purity and affinity for a target antigen:

General Formula 1

(SEQ ID NO: 7)

$VDX_3KX_5X_6KEX_9X_{10}X_{11}AX_{13}X_{14}EIX_{17}X_{18}LPNLTX_{24}X_{25}$ $QX_{27}X_{28}AFIX_{32}X_{33}LX_{35}DDPSQSX_{42}X_{43}LLX_{46}$ $EAKKLNDSQAPK,$ wherein $X_3$, $X_5$, $X_6$, $X_9$, $X_{10}$, $X_{11}$, $X_{13}$, $X_{14}$, $X_{17}$, $X_{18}$, $X_{24}$, $X_{25}$, $X_{27}$, $X_{28}$, $X_{32}$, $X_{33}$, $X_{35}$, $X_{42}$, $X_{43}$, and $X_{46}$ each are independently any amino acid residue, $X_3$ is selected from A and N;

$X_5$ is selected from F and Y;

$X_6$ is selected from A and N;

$X_9$ is selected from A, B, C, E, G, H, K, L, M, S, T, V, and Q;

$X_{10}$ is selected from A, B, F, G, H, K, L, M, P, Q, R, S, T, V, W, and Y;

$X_{11}$ is selected from A, B, C, D, E, F, G, H, I, K, L, M, N, P, Q, R, V, W, and Y;

$X_{13}$ is selected from C, D, F, G, H, I, L, P, Q, S, T, and V;

$X_{14}$ is selected from A, C, D, E, F, H, I, K, L, M, N, P, Q, R, S, T, V, W, and Y;

$X_{17}$ is selected from A, B, E, F, G, H, I, L, M, P, Q, R, T, V, W, and Y;

$X_{18}$ is selected from A, D, E, F, G, H, I, K, L, N, R, S, T, V, W, and Y;

$X_{24}$ is selected from A, C, D, E, F, G, I, K, L, M, N, P, Q, R, S, T, V, and W;

$X_{25}$ is selected from A, C, D, E, G, H, I, K, L, M, N, Q, R, S, T, V, W, and Y;

$X_{27}$ is selected from A, C, G, H, I, K, L, M, P, Q, R, S, T, V, and W;

$X_{28}$ is selected from A, B, E, F, G, I, K, L, M, N, P, Q, R, S, T, V, and Y;

$X_{32}$ is selected from A, D, F, G, I, L, M, N, Q, R, S, T, V, and W;

$X_{33}$ is selected from K and S;

$X_{35}$ is selected from A, D, E, F, G, H, I, K, L, M, P, Q, R, S, T, V, W, and Y;

$X_{42}$ is selected from A and S;

$X_{43}$ is selected from A, C, and S; and $X_{46}$ is selected from D, E, and S.

The amino acid residues expressed the form of $X_y$ as defined in the general formula herein denotes the positions of amino acid residues that provide specific binding properties for a target antigen of a polypeptide consisting of an amino acid sequence of the general formula, and $X_y$ may be selected from all of 20 natural amino acid residues, and y means corresponding to the y-th position in the amino acid sequence of the general formula.

The amino acid residues that are not defined in the form of $X_y$ herein are referred to as scaffold amino acids or scaffolds. The scaffold amino acids denote amino acid sequences that are distinguished from the $X_y$-form random amino acids imparting binding affinity to a target antigen of the polypeptide of the present invention, and give structural stability as a polypeptide or a polypeptide complex of the present invention.

In accordance with another aspect of the present invention, there is provided a polypeptide including an amino acid sequence of General Formula 2 below, wherein i) T is substituted with N at the 23rd amino acid position in General Formula 2 below, ii) S is substituted with A at the 54th amino acid position in General Formula 2 below, and iii) T and S are N and A at the 23rd and 54th amino acid positions in General Formula 2, respectively, whereby glycosylation is prevented upon the production of the polypeptide in eukaryotic cells and thus the polypeptide is improved in protein purity and affinity for a target antigen:

```
General Formula 2
                                    (SEQ ID NO: 8)
AEAKYAKEX9X10X11AIX17X18LPNLTX24X25

QX27X28AFIX32X33LX35DDPSQSX42X43LL

X46EAKKLNDSQAPK,
``` wherein $X_9$, $X_{10}$, $X_{11}$, $X_{17}$, $X_{18}$, $X_{24}$, $X_{25}$, $X_{27}$, $X_{28}$, $X_{32}$, $X_{33}$, $X_{35}$, $X_{42}$, $X_{43}$, and $X_{46}$ each are independently any amino acid residue, and are as defined in General Formula 1 above.

According to a specific embodiment of the present invention, $X_9$, $X_{10}$, $X_{11}$, $X_{17}$, $X_{18}$, $X_{24}$, $X_{25}$, $X_{27}$, $X_{28}$, $X_{32}$, $X_{33}$, $X_{35}$, $X_{42}$, $X_{43}$, and $X_{46}$ each are independently any amino acid residue, and $X_9$ may be selected from E, G, and M;

$X_{10}$ may be selected from A, F, H, K, Q, R, S, Wand Y;

$X_{11}$ may be selected from A, D, E, F, H, I, K, L, M, N, Q, R, S, T, V, and Y;

$X_{17}$ may be selected from A, B, E, F, G, H, I, L, M, P, Q, R, T, V, W, and Y;

$X_{18}$ may be selected from A, I, K, L, M, N, R, S, T, and V;

$X_{24}$ may be selected from A, I, T, and V;

$X_{25}$ may be selected from D, E, G, H, K, N, Q, R, S, and T;

$X_{27}$ may be selected from I, L, M, R, T, and V;

$X_{28}$ may be selected from A, S, T, and V;

$X_{32}$ may be selected from I, M, Q, S, T, V, and W;

$X_{33}$ may be selected from K and S; and $X_{35}$ may be selected from F, L, M, S, V, and Y.

The polypeptide of the present invention may be changed to have affinity for any antigen through a random arrangement change of the Xy sequence. In that sense, the present invention provides a modified scaffold, which is not a known scaffold per se capable of binding to a target antigen but a scaffold improved in purity and affinity for a target antigen by substitution of an amino acid residue at a specific position with another amino acid residue.

As described above, the amino acids to be substituted are T at the 23rd amino acid position and S at the 54th amino acid position in General Formula 1 or 2. As for the amino acid residues, T is substituted with N at the 23rd amino acid position; S is substituted with A at the 54th amino acid position; or T and S are substituted with N and A at the 23rd and 54th amino acid positions, respectively.

Such amino acid residue substitutions allow the polypeptides (Affibody molecules) consisting of the sequences of the general formulas of the present invention to be improved in polypeptide purity and affinity for a target antigen since glycosylation, a kind of post translational modification (PTM), is prevented on N at the 14th amino acid position and N at the 52nd amino acid position, even when the polypeptides (Affibody molecules) are expressed in host cells using prokaryotic cells (e.g., *E. coli*) as well as host cells using eukaryotic cells (e.g., CHO cells).

Advantages of the present invention distinguished from the prior art will be described through specific embodiments.

When the polypeptide consisting of the amino acid sequence of SEQ ID NO: 1 of the present invention is expressed in eukaryotic cells, for example HEK293F cells, as host cells, glycosylation occurs on asparagine (Asn, N) at positions 21 and 52 in SEQ ID NO: 1. The glycosylation at the amino acid positions degrades the binding strength of the polypeptide (Affibody molecule) of the present invention to IL-6.

However, according to an example of the present invention, the glycosylation occurring on asparagine at positions 21 and 52 in SEQ ID NO: 1 is prevented when i) threonine (Thr, T), which is the amino acid at position 23 in the amino acid sequence of SEQ ID NO: 1, is substituted with asparagine (Asn, N) like in SEQ ID NO: 2 or SEQ ID NO: 4; and ii) serine (Ser, S), which is the amino acid at position 54 in the amino acid sequence of SEQ ID NO: 1, is substituted with alanine (Ala, A) like in SEQ ID NO: 3 or 4.

In cases where the polypeptide consisting of the amino acid sequence of any one of SEQ ID NO: 2 to SEQ ID NO: 4, instead of SEQ ID NO: 1, is produced in eukaryotic cells, glycosylation is prevented, leading to an improvement in protein purity (homogeneity) (FIGS. 2 to 4). Furthermore, such a polypeptide has enhanced binding ability to IL-6 (FIGS. 5 to 7).

Therefore, according to an embodiment of the present invention, the polypeptide consisting of the amino acid sequence of General Formula 1 or General Formula 2 may consist of the amino acid sequence of any one of SEQ ID NO: 2 to SEQ ID NO: 4, and in such a case, the target antigen of the polypeptide is interleukin-6 (IL-6), and the polypeptide has excellent affinity for IL-6.

The "interleukin 6 (IL-6)" is abbreviated as IL-6, and refers to a glycoprotein of a molecular weight of about 210.000 isolated as B-cell stimulating factor 2 (BSF-2) that induces the final differentiation of B cells into antibody-producing cells. IL-6 is a cytokine, which is produced from a variety of cells, such as T lymphocytes, B lymphocytes, macrophages, and fibroblasts, and is a molecule the same as interferon β2 (IFN-β2). IL-6 is known to be involved in immune response, proliferation and differentiation of hematopoietic and nervous system cells, acute responses, and the like. Human IL-6 is composed of 212 amino acid residues containing 28 signal peptides, and mouse IL-6 is composed of 211 amino acid residues containing 24 signal peptides. Excessive production of IL-6 is known to be deeply involved in the onset several types of immune dysfunction, inflammatory diseases, and lymphatic tumors.

In accordance with still another aspect of the present invention, there is provided a polypeptide complex including: i) the polypeptide of any one of claims 1 to 3; and ii) an antibody or an antigen-binding fragment thereof, wherein i) and ii) are linked to each other.

In such a case, the polypeptide complex has a multimeric form in which respective monomers of a polypeptide and an antibody or an antigen-binding fragment thereof are linked to each other. The polypeptide complexes of the present invention are linked to each other via a covalent linkage. According to an embodiment of the present invention, the polypeptide complex may be implemented in the form of a fusion protein or a conjugate.

As used to indicate an aspect of the present invention, the term "complex" is used to designate two or more linked polypeptide chains, of which one component is a polypeptide (Affibody molecule) having affinity for a target antigen (e.g., IL-6) as defined above and the other component is an antibody or an antigen-binding fragment thereof specifically binding the target antigen. The "complex" is used to designate two or more polypeptides, which are linked via a covalent linkage, for example, through the expression of two or more polypeptide chains into a recombinant fusion protein, or are linked by chemical conjugation.

According to an embodiment of the present invention, the polypeptide complex may be formed by a linkage of: IL-6 binding polypeptide consisting of the amino acid sequence of any one of SEQ ID NO: 2 to SEQ ID NO: 4; and an antibody or an antigen-binding fragment thereof. The IL-6 binding polypeptide (Affibody molecule) constituting the polypeptide complex may be fused and linked to the N-terminus and/or C-terminus of a heavy chain/light chain region of the antibody or the antigen-binding fragment thereof.

For example, the IL-6 binding polypeptide consisting of SEQ ID NO: 2 to SEQ ID NO: 4 may be linked to only the N-terminus of the heavy chain, only the N-terminus of the light chain thereof, only the C-terminus of the heavy chain, only the C-terminus of the light chain, both the N-terminus and C-terminus of the heavy chain, both the N-terminus and C-terminus of the light chain, only the C-terminus of the light chain and the N-terminus of the heavy chain, or only the C-terminus of the heavy chain and the N-terminus of the light chain in the antibody or the antigen-binding fragment thereof.

According to another embodiment of the present invention, the IL-6 binding polypeptide (Affibody molecule) and the antibody or the antigen-binding fragment thereof in the polypeptide complex may be directly linked to each other, or indirectly linked to each other via a linker (e.g., amino acid linker).

A person skilled in the art could conceive that a linker may be used between functional moieties to be usually fused in the production of a fusion protein and examples of different kinds of linkers having different characteristics are a flexible amino acid linker, a non-flexible linker, and a cleavable amino acid linker. The linkers have been used for the purpose of increasing expression levels, improving biological activity, and enabling targeting, or changing pharmacokinetics of the fusion protein, or in order to increase stability and improve folding property of the fusion protein.

Therefore, according to a specific embodiment of the present invention, the complex may further contain at least one linker, for example, at least one linker selected from flexible amino acid linkers, non-flexible linkers, and cleavable amino acid linkers. According to a most specific embodiment of the present invention, the linker is arranged between the Affibody molecule and the antibody or the antigen-binding fragment thereof.

According to still another embodiment of the present invention, the complex may contain at least one additional amino acid at the C-terminus and/or N-terminus. The additional amino acid residue may be separately or collectively added for the purpose of improving, for example, productivity, purification, in vivo or in vitro stabilization, coupling with the complex, or detection. For example, a cysteine residue may be added to the C-terminus and/or N-terminus of the complex. The additional amino acid residue may provide a "tag" for purification or polypeptide detection and, for example, may provide a tag, such as $His_6$ tag, $(HisGlu)_3$ tag ("HEHEHE" tag), "myc" (c-myc) tag, or "FLAG" tag for an interaction with an antibody specific to the tag or for immobilized metal affinity chromatography (IMAC) for $His_6$ tag.

The additional amino acids as described above may be linked to i) the IL-6 binding polypeptide and ii) the complex of the IL-6 binding polypeptide and the antibody or the antigen-binding fragment thereof defined herein by means of chemical conjugation, via the expression of i) the IL-6 binding polypeptide and ii) the complex of the IL-6 binding polypeptide and the antibody or the antigen-binding fragment thereof as a fusion protein, or either directly, or indirectly via a linker (e.g., amino acid linker).

As used herein, the antibody or antigen-binding fragment thereof encompasses not only full-length or intact polyclonal or monoclonal antibodies, but also antigen-binding fragments thereof (e.g., Fab, Fab', F(ab')₂, Fab3, Fv, and variants thereof), fusion proteins containing one or more antibody portions, humanized antibodies, chimeric antibodies, minibodies, diabodies, triabodies, tetrabodies, linear antibodies, single-chain antibodies, multi-specific antibodies (e.g., bispecific antibodies), and any other modified configuration of the immunoglobulin molecule that contains an antigen recognition site of the required specificity, including glycosylation variants of antibodies, amino acid sequence variants of antibodies, and covalently modified antibodies. Specific examples of the modified antibodies and antigen-binding fragments thereof include nanobodies, AlbudAbs, DARTs (dual affinity re-targeting), BITEs (bispecific T-cell engager), TandAbs (tandem diabodies), DAFs (dual acting Fab), two-in-one antibodies, SMIPs (small modular immunopharmaceuticals), FynomAbs (fynomers fused to antibodies), DVD-Igs (dual variable domain immunoglobulin), CovX-bodies (peptide modified antibodies), duobodies, and triomAbs. This listing of such antibodies and antigen-binding fragments thereof is not limited thereto.

A full-length antibody contains two heavy chains and two light chains. Each heavy chain contains a heavy chain variable region ($V_H$) and first, second and third constant regions ($C_H1$, $C_H2$ and $C_H3$). Each light chain contains a light chain variable region ($V_L$) and a light chain constant region ($C_L$). Antibodies may be divided into different classes according to the amino acid sequence of the constant region of the light chain. There are six major classes of antibodies: IgA, IgD, IgE, IgG, IgM, and IgY. Out of these, some may be further divided into subclasses (isotypes), e.g., IgG1, IgG2, IgG3, IgG4, IgA1, and IgA2. As used herein, the term "full-length antibody" refers to an antibody of any class, such as IgD, IgE, IgG, IgA, IgM, or IgY (or any sub-class thereof). The subunit structures and three-dimensional configurations of different classes of antibodies are well known to a person skilled in the art.

As used herein, the term "antigen-binding fragment" is an antibody molecule, a portion or region thereof, or a derivative thereof, which retains all or a significant part of the antigen binding of the corresponding full-length antibody. The antigen-binding fragment may contain the heavy chain variable region ($V_H$), the light chain variable region ($V_L$), or both. Each of the $V_H$ and $V_L$ typically contains complementarity determining regions CDR1, CDR2, and CDR3. The three CDRs in $V_H$ or $V_L$ are flanked by framework regions (FR1, FR2, FR3 and FR4).

As described above, examples of antigen-binding fragments include, but are not limited to:

(1) a Fab fragment, which is a monovalent fragment having a $V_L$-$C_L$ chain and a $V_H$-$C_H1$ chain; (2) a Fab' fragment, which is a Fab fragment with the heavy chain hinge region; (3) a F(ab')₂ fragment, which is a dimer of Fab' fragments joined by the heavy chain hinge region, for example, linked by a disulfide bridge at the hinge region; (5) an Fv fragment, which is the minimum antibody fragment having the $V_L$ and $V_H$ domains of a single arm of an antibody; (6) a single chain Fv (scFv) fragment, which is a single polypeptide chain in which the $V_H$ and $V_L$ domains of an scFv are linked by a peptide linker; (7) an (scFv) 2, which contains two $V_H$ domains and two $V_L$ domains, which are associated through the two $V_H$ domains via disulfide bridges; and (8) domain antibodies, which can be antibody single variable domain ($V_H$ or $V_L$) polypeptides that specifically bind antigens.

The antigen-binding fragments can be prepared by routine methods used in the art. For example, $F(ab')_2$ fragments can be produced by pepsin digestion of a full-length antibody molecule, and Fab fragments can be produced by reducing the disulfide bridges of $F(ab')_2$ fragments. Alternatively, the fragments can be prepared via recombinant technology by expressing the heavy and light chain fragments in suitable host cells (e.g., *E. coli*, yeast, mammalian, plant, or insect cells) and assembling these to form desired antigen-binding fragments in vivo or in vitro. A single-chain antibody can be prepared via recombinant technology by linking a nucleotide sequence encoding a heavy chain variable region and a nucleotide sequence encoding a light chain variable region. For example, a flexible linker may be incorporated between the two variable regions.

As used herein, the term "monoclonal antibodies" refers to antibodies having monovalent affinity, meaning that each antibody molecule in a sample of the monoclonal antibody binds to the same epitope on the antigen On the other hand, the term "polyclonal antibodies" as used herein refers to a collection of antibodies that react against a specific antigen, but in the collection, such antibodies may be different antibody molecules that, for example, react with different epitopes on the antigen. Polyclonal antibodies can be typically produced by inoculation of a suitable animal, and can be isolated from the serum of the animal. Monoclonal antibodies are made by identical immune cells, which are clones of a unique parent cell (for example, a hybridoma cell line). As used herein, the term "human antibody" refers to an antibody having variable and constant regions substantially corresponding to an antibody obtained or originated from humans. As used herein, the term "chimeric antibodies" refers to recombinant or genetically engineered antibodies, for example, mouse monoclonal antibodies, which contain polypeptides or domains from different species, or human antibodies, which are introduced to reduce the immunogenicity of antibodies. The term "humanized antibodies" refers to antibodies from non-human species, of which protein sequences have been modified to increase their similarity to antibody variants produced naturally in humans, in order to reduce immunogenicity.

Since the complex defined in the present invention is composed of the IL-6 binding polypeptide and the antibody or antigen-binding fragment thereof, the complex may not only bind to IL-6, but may also bind specifically to at least one additional antigen.

According to an embodiment of the present invention, the additional antigen may be associated with a disease or disorder of the immune system. In another embodiment, the additional antigen may be associated with cancer. Therefore, in one embodiment, the complex as defined in the present invention is provided, wherein the antibody or antigen-binding fragment thereof has affinity for an additional antigen, for example, an antigen associated with a disease or disorder of the immune system, or associated with cancer.

According to a specific embodiment of the present invention, the additional antigen may include antigens associated with IL-6 related diseases as well as antigens associated with IL-6 related diseases. According to still another embodiment, the additional antigen to which the polypeptide complex of the present invention can specifically bind may be selected from the group consisting of angiogenin 2 (Ang-2), vascular endothelial growth factor, tumor necrosis factor, tumor necrosis factor ligands, super family members TNF-α, TNFSF11, TNFSF13, TNFSF13B, TNFSF14, and TNFSF15, insulin-like growth factor, interleukin 1α, interleukin 1β, interleukin 10, interleukin 17A, interleukin 12, interleukin 23, interleukin 33, granulocyte macrophage colony-stimulating factor, granulocyte colony stimulating factor, lipopolysaccharide, toll-like receptor 4, nerve growth factor, chemokine C-C motif ligand 19, chemokine C-C motif ligand 21, chemokine C-C motif ligand 4, and IFN-α, but is not limited thereto.

According to another specific embodiment of the present invention, ii) the antibody or the antigen-binding fragment thereof may contain the amino acid sequence of SEQ ID NO: 5, and in such a case, the target antigen thereof is TNF-α.

In addition, the target antigens to which i) the polypeptide and ii) the antibody or the antigen-binding fragment thereof specifically bind may be identical antigens or different antigens.

When the target antigens of i) the polypeptide and ii) the antibody or the antigen-binding fragment thereof are identical to each other, the polypeptide complex shows improved affinity for the corresponding antigen, and when the target antigens of i) the polypeptide and ii) the antibody or antigen-binding fragment thereof are different from each other, the polypeptide complex has multi-specificity, or is able to specifically bind to two or more kinds of antigens, and thus can target an additional antigen, and therefore such a polypeptide complex is useful.

According to an embodiment of the present invention, the polypeptide complex may be implemented in the form of a fused protein or a conjugate.

Therefore, the polypeptide (Affibody molecule) and the antibody or the antigen-binding fragment thereof may be linked by means of chemical conjugation (using known organic chemistry methods) or by any other means (for example, via the expression of the complex as a fusion protein, or either directly, or indirectly via a linker (e.g., an amino acid linker)).

According to a specific embodiment of the present invention, i) the polypeptide and ii) the antibody or the antigen-binding fragment thereof of the polypeptide complex are linked to each other via at least one linker.

In such a case, the linker may consisting of an amino acid sequence represented by the general formula (GnSm)p or (SmGn)p, wherein n, m, and p each are independent;
n is an integer of 1 to 7;
m is an integer of 0 to 7;
the sum of n and m is an integer of 8 or smaller, and
p is an integer of 1 to 7.

According to another specific embodiment of the present invention, n=1 to 5 and m=0 to 5 in the linker. In a more specific embodiment, n=4 and m=1. In a still more specific embodiment, the linker is $(GGGGS)_3$ (SEQ ID NO: 15). In still another embodiment, the linker is GGGGS (SEQ ID NO: 16). In still another embodiment, the linker is VDGS (SEQ ID NO: 17). In still another embodiment, the linker is ASGS (SEQ ID NO: 18).

In the following contents, TNF is used as an illustrative example of the additional antigen as described above and thus should not be construed as limiting the scope. Therefore, the following method for measuring affinity may be used to measure the affinity of an antibody for any other suitable additional antigen, and is not necessarily limited to the method described below, and a person skilled in the art can use various usable methods.

As used herein, the terms "IL-6 binding", "binding affinity for IL-6", "TNF binding", and "binding affinity for TNF" refer to a property of a polypeptide, or the complex as defined herein, which may be tested by, for example, ELISA or surface plasmon resonance (SPR). For example, binding affinity may be tested through an experiment in which the polypeptide samples of the present invention are captured on antibody-coated ELISA plates and biotinylated IL-6 (or biotinylated TNF) is added, followed by streptavidin conjugated HRP. By using a multi-well plate reader (e.g., Victor3 (Perkin Elmer)), TMB substrate is added and the absorbance at 450 nm is measured. A person skilled in the art may interpret the results obtained through such experiments for establishing qualitative measurement of the binding affinity of the complex for IL-6 (or TNF). If the quantitative measurement is to be desired, for example, the $EC_{50}$ value for interaction is to be determined, ELISA may be used. The response of the polypeptide against a dilution series of biotinylated IL-6 (or biotinylated TNF) is measured using ELISA as described above. A person skilled in the art would interpret the results obtained by such experiments, and would calculate $EC_{50}$ values from the results by using, for example, GraphPad Prism 5 and non-linear regression.

The IL-6 binding affinity or the affinity for an additional antigen (e.g., TNF) may also be measured through a surface plasmon resonance (SPR) experiment. IL-6 (or TNF) or a fragment thereof is immobilized on a sensor chip of an SPR instrument, and a sample containing the complex to be tested is allowed to pass over the chip. Alternatively, the complex to be tested is immobilized on a sensor chip of the instrument, and a sample containing IL-6 (or TNF) or a fragment thereof is allowed to pass over the chip. A person skilled in the art would interpret the results obtained through such experiments for establishing at least qualitative measurement of the binding affinity of the complex for IL-6 (or TNF). If the quantitative measurement is to be desired, for example, the $K_D$ value for interaction is to be determined, SPR may be used. The binding values may be defined by an instrument, such as Biacore (GE Healthcare) or ProteOn XPR 36 (Bio-Rad). IL-6 (or TNF) is suitably immobilized on a sensor chip of the instrument, and samples of the complex with determined affinity are prepared by serial dilution, and then injected in a random order. A person skilled in the art would calculate $K_D$ values from the results by using, for example, the 1:1 Langmuir binding model of the BIAevaluation 4.1 software, or other suitable software provided by the instrument manufacturer.

According to a specific embodiment of the present invention, the antibody or antigen-binding fragment thereof, which is one component of the polypeptide complex of the present invention, may be an antibody consisting of the amino acid sequence of SEQ ID NO: 5. In such a case, the polypeptide complex of the present invention additionally has binding affinity for TNF-α in addition to IL-6.

In accordance with an aspect of the present invention, there is provided a pharmaceutical composition containing:

(a) a polypeptide represented by General Formula 1 or General Formula 2 and improved in purity and antigen affinity by the substitution of an amino acid residue at a specific position; and (b) a pharmaceutically acceptable carrier.

In accordance with another aspect of the present invention, there is provided a pharmaceutical composition containing: (a) a polypeptide complex, in which i) the polypeptide represented by General Formula 1 or General Formula 2 and improved in purity and antigen affinity by the substitution of an amino acid residue at a specific position and ii) an antibody or an antigen-binding fragment thereof are linked to each other, and (b) a pharmaceutically acceptable carrier.

The diseases that could be prevented or treated by the pharmaceutical composition of the present invention vary depending on the kind of antigen to which the polypeptide or the polypeptide complex of the present invention can bind with affinity. For example, when the polypeptide or the polypeptide complex, which is an active ingredient of the pharmaceutical composition of the present invention, has affinity for an antigen associated with an IL-6 related disease, the pharmaceutical composition of the present invention can treat the IL-6 related disease. The IL-6 related disease is illustrative, and thus it would be obvious to a person skilled in the art that the scope of the present invention is not limited thereto.

As used herein, the term "IL-6 related disease" refers to any disorder, disease, or condition in which IL-6 plays a regulatory role in the signaling pathway.

In one embodiment of the present invention, there is provided a complex or composition herein for use in the treatment of an IL-6 related disease. Non-limiting lists of the IL-6 related disease for the treatment, of which the complex or composition herein may be useful, include: inflammatory diseases, autoimmune diseases, infectious diseases, cancer, neoplastic diseases, diabetes, depressive neurological diseases, rheumatoid arthritis, juvenile rheumatoid arthritis, juvenile idiopathic arthritis, systemic juvenile idiopathic arthritis, vasculitis, psoriatic arthritis, psoriasis, ankylosing spondylitis, chronic inflammatory bowel diseases, such as Crohn's disease and ulcerative colitis, Grave's disease, Behçet's disease, uveitis, giant cell arteritis, multiple sclerosis, systemic sclerosis, systemic lupus erythematosus, polymyositis, polymyalgia rheumatic, asthma, chronic obstructive pulmonary diseases, relapsing polychondritis, pancreatitis, peritonitis, nephritis, Kawasaki's disease, Sjögren's syndrome, adult Still's disease, colitis associated cancer, kidney cancer, prostate cancer, malignant lymphoma, multiple myeloma, Castleman's disease, breast cancer, lung cancer, Alzheimer's disease, HIV, diabetes, sepsis, cachexia, myelodysplastic syndrome (MDS), liver cirrhosis, graft versus host disease, myocardial infarction, endometriosis, and osteoporosis.

In a certain particular embodiment, the disease is selected from the group consisting of rheumatoid arthritis, juvenile rheumatoid arthritis, juvenile idiopathic arthritis, or systemic juvenile idiopathic arthritis. In a specific embodiment, the disease is rheumatoid arthritis.

In still another embodiment, the disease is a chronic inflammatory bowel disease, for example, Crohn's disease and ulcerative colitis.

In still another embodiment, the disease is cancer or a neoplastic disease, for example, cancer or a neoplastic disease selected from the group consisting of colitis associated cancer, kidney cancer, prostate cancer, malignant lymphoma, multiple myeloma, breast cancer, and lung cancer.

In a certain particular embodiment, the disease includes B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), Null-acute lymphoblastic leukemia, non-Hodgkin lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin lymphoma.

In addition, the disease includes autoimmune diseases and inflammatory diseases associated with inappropriate or enhanced B cell number and/or activation. Examples of the autoimmune diseases and inflammatory diseases include multiple sclerosis, rheumatoid arthritis, and systemic lupus erythematosus (SLE).

In still another embodiment, the disease is selected from the group consisting of Alzheimer's disease, HIV, diabetes, sepsis, cachexia, myelodysplastic syndrome (MDS), liver cirrhosis, graft versus host disease, myocardial infarction, endometriosis, and osteoporosis.

The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in Remington's Pharmaceutical Sciences (19th ed., 1995).

The pharmaceutical composition of the present invention may be administered orally or parenterally, for example, intravenous injection, subcutaneous injection, intramuscular injection, intraperitoneal injection, intrasternal injection, intratumoral injection, topical administration, intranasal administration, intrapulmonary administration, and rectal administration.

The appropriate dose of the pharmaceutical composition of the present invention varies depending on factors, such as a formulating method, a manner of administration, patient's age, body weight, gender, and morbidity, food, a time of administration, a route of administration, an excretion rate, and response sensitivity. An ordinarily skilled practitioner can easily determine and prescribe an effective dose for desired treatment or prevention. According to a preferable embodiment of the present invention, the daily dose of the pharmaceutical composition of the present invention is 0.0001-100 mg/kg. As used herein, the term "pharmaceutically effective amount" refers to an amount sufficient to prevent or treat the above-described diseases.

As used herein, the term "prevention" refers to a prophylactic or protective treatment of a disease or a disease condition. As used herein, the term "treatment" refers to a reduction, suppression, amelioration, or eradication of a disease condition.

The pharmaceutical composition of the present invention may be formulated into a unit dosage form or may be prepared in a multi-dose container by using a pharmaceutically acceptable carrier and/or excipient according to a method that can be easily implemented by a person having an ordinary skill in the art to which the present invention pertains. Here, the formulation may be in the form of a solution in an oily or aqueous medium, a suspension, an emulsion, an extract, a pulvis, a suppository, a powder, granules, a tablet, or a capsule, and may further contain a dispersant or a stabilizer.

Since the pharmaceutical composition of the present invention contains the above-described polypeptide or polypeptide complex of the present invention as an active ingredient, the overlapping descriptions thereof are omitted to avoid excessive complication of the specification due to repetitive descriptions thereof.

In accordance with still another aspect of the present invention, there is provided a method for prevention or treatment of cancer or an IL-6 related disease, the method including administering the foregoing pharmaceutical composition of the present invention to a subject.

As used herein, the term "administration" or "administer" refers to the direct administration of a therapeutically effective amount of the composition of the present invention to a subject (individual) in need of the composition, thereby forming the same amount thereof in the body of the subject.

The term "therapeutically effective amount" of the composition refers to the content of the composition, which is sufficient to provide a therapeutic or prophylactic effect to a subject, to which the composition is to be administered, and thus the term is meant to encompass "prophylactically effective amount". As used herein, the term "subject" includes, but is not limited to, a human being, mouse, rat, guinea pig, dog, cat, horse, cow, pig, monkey, chimpanzee, baboon, or rhesus monkey. Specifically, the subject of the present invention is a human being.

Since the method for the prevention or treatment of cancer or an IL-6 related disease of the present invention includes administering the pharmaceutical composition according to an aspect of the present invention, the overlapping descriptions thereof are omitted to avoid excessive complication of the specification.

In accordance with still another aspect of the present invention, there is provided a nucleic acid consisting of a nucleotide sequence encoding the polypeptide, which is represented by General Formula 1 or 2 and improved in purity and antigen affinity through the substitution of an amino acid residue at a specific position.

In accordance with still another aspect of the present invention, there is provided a nucleic acid consisting of a nucleotide sequence encoding the polypeptide complex formed by the linkage of the polypeptide and the antibody or the antigen-binding fragment thereof.

In an embodiment of the present invention, it would be obvious to a person skilled in the art that the nucleotide sequence encoding i) the polypeptide or ii) the polypeptide complex containing the polypeptide and the antibody or antigen-binding fragment thereof specifically binding to any target antigen is a nucleotide sequence encoding the amino acid sequence constituting the polypeptide or the polypeptide complex, and is not limited to any particular nucleotide sequence.

The reason is that even if the nucleotide sequence undergoes mutation, the expression of the mutated nucleotide sequence into a protein may not cause a change in the protein sequence. This is called the degeneracy of codons. Therefore, the nucleotide sequence includes nucleotide sequences containing functionally equivalent codons, codons encoding the same amino acids (e.g., due to the degeneracy of codons, the number of codons for arginine or serine being six), or codons containing biologically equivalent amino acids.

As used herein, the term "nucleic acid" refers to comprehensively including DNA (gDNA and cDNA) and RNA molecules, and the nucleotide as a basic constituent unit in the nucleic acid molecule includes naturally occurring nucleotides, and analogues with modified sugars or bases (Scheit, Nucleotide Analogs, John Wiley, New York (1980); and Uhlman & Peyman, Chemical Reviews, 90:543-584 (1990)).

Considering the above-described mutation having biologically equivalent activity, it should be construed that the nucleic acid molecules of the present invention encoding the amino acid sequences of SEQ ID NO: 2 to SEQ ID NO: 4 also include sequences showing substantial identity therewith. The substantial identity refers to a sequence showing at least 60%, more preferably at least 70%, still more preferably at least 80%, still more preferably at least 90% nucleotide, and most specifically at least 95% identity when the sequence of the present invention and any other sequence are correspondingly aligned as much as possible and the aligned sequence is analyzed using algorithms commonly used in the art. Methods of alignment for sequence comparison are known in the art. Various methods and algorithms for alignment are disclosed in Smith and Waterman, *Adv. Appl. Math.* 2: 482 (1981); Needleman and Wunsch, *J. Mol. Bio.* 48: 443 (1970); Pearson and Lipman, *Methods in Mol. Biol.* 24:307-31 (1988); Higgins and Sharp, *Gene* 73:237-44 (1988); Higgins and Sharp, *CABIOS* 5:151-3 (1989); Corpet et al., *Nuc. Acids Res.* 16:10881-90 (1988); Huang et al., *Comp. Appl. BioSci.* 8:155-65 (1992); and Pearson et al., *Meth. Mol. Biol.* 24:307-31 (1994), but are not limited thereto. Specifically, in the present invention, ClustalX and neighbor-joining (NJ) algorithms are used. The NCBI Basic Local Alignment Search Tool (BLAST; Altschul, et al., *J. Mol. Biol.* 215:403-10 (1990)) is available from, for example, the NBCI (National Center for Biological Information), and can be used in connection with sequence analysis programs, such as blastp, blasm, blastx, tblastn and tblastx, on the Internet.

In accordance with an aspect of the present invention, there is provided a method for producing a polypeptide improved in protein purity and affinity for an antigen by preventing glycosylation, the method including:

(a) inserting the nucleic acid consisting of a nucleotide sequence encoding the polypeptide into an expression vector;

(b) transforming the expression vector into a host cell; and (c) culturing the host cell to obtain a polypeptide.

In accordance with another aspect of the present invention, there is provided a method for producing a polypeptide complex improved in protein purity and affinity for an antigen by preventing glycosylation, the method including:

(a) inserting the nucleic acid consisting of a nucleotide sequence encoding the polypeptide complex into an expression vector;

(b) transforming the expression vector into a host cell, which is an eukaryotic cell; and (c) culturing the host cell to obtain a polypeptide complex.

According to an embodiment of the present invention, the expression vector is a recombinant vector for host cell expression, into which (a) a nucleotide sequence encoding i) a polypeptide (Affibody molecule), such as the amino acid sequence of any one of SEQ ID NO: 2 to SEQ ID NO: 4 or ii) a complex of the polypeptide and an antibody or antigen-binding fragment thereof is inserted, wherein the vector contains: (b) a promoter, which is operatively linked to the nucleotide sequence and forms an RNA molecule in host cells; and (c) a poly A signal sequence, which acts on the host cells to cause polyadenylation of the 3'-terminus of the RNA molecule.

As used herein, the term "operatively linked" refers to a functional linkage between a nucleic acid expression control sequence (e.g., a promoter, a signal sequence, or an array of transcription regulation factor binding sites) and another nucleic acid sequence, whereby the control sequence controls the transcription and/or translation of the another nucleic acid sequence.

The vector system of the present invention can be constructed by various methods known in the art, and a specific method thereof is disclosed in Sambrook, et al., Molecular Cloning, A Laboratory Manual, Cold Spring Harbor Laboratory Press (2001), the teachings of which are incorporated herein by reference.

The vector of the present invention may be typically constructed as a vector for cloning or a vector for expression. In addition, the vector of the present invention may be constructed by using prokaryotic or eukaryotic cells as a host.

When the vector of the present invention is an expression vector and prokaryotic cells are used as a host, the vector generally contains a strong promoter capable of implementing transcription (e.g., pL$^\lambda$ promoter, trp promoter, lac promoter, 17 promoter, tac promoter, etc.), a ribosome binding site for initiation of translation, and a transcriptional/translational termination sequence. In cases where *E. coli* is used as a host cell, the promoter and operator sites for the *E. coli* tryptophan biosynthesis pathway (Yanofsky, C., J. Bacteriol., 158:1018-1024 (1984) and the leftward promoter from phage λ (pLA promoter, Herskowitz, I. and Hagen, D., *Ann. Rev. Genet.*, 14:399-445 (1980) may be used as a control region.

Meanwhile, the vector usable in the present invention may be constructed by manipulating plasmids (e.g., pSK349, pSC101, ColE1, pBR322, pUC8/9, pHC79, pGEX series, pET series, and pUC19, etc.), phages (e.g., λgt·λ4B, λ-Charon, λΔz1, and M13, etc.), or a viruses (e.g., SV40, etc.), which are often used in the art.

The vector of the present invention may be fused to another sequence to facilitate the purification of a polypeptide expressed therefrom. Examples of the sequence to be used for the fusion include, for example, glutathione S-transferase (Pharmacia, USA), maltose binding protein (NEB, USA), FLAG (IBI, USA), and 6× His (hexahistidine; Quiagen, USA). Due to the additional sequence for purification, the protein expressed in the host is promptly and easily purified through affinity chromatography.

The vector of the present invention includes, as a selective marker, an antibiotic-resistant gene that is ordinarily used in the art, and may include resistant genes against ampicillin, gentamycin, carbenicillin, chloramphenicol, streptomycin, kanamycin, geneticin, neomycin, and tetracycline.

Meanwhile, when the vector of the present invention is an expression vector and an eukaryotic cell is used as a host, a promoter derived from a genome of a mammalian cell (e.g., a metallothionein promoter) or a promoter derived from an mammalian virus (e.g., adenovirus late promoter, vaccinia virus 7.5 K promoter, SV40 promoter, cytomegalovirus promoter, HSV tk promoter) may be used, and the vector generally has a polyadenylation sequence as a transcription termination sequence.

Optionally, the vector may additionally deliver a gene encoding a reporter molecule (e.g., luciferase and glucuronidase).

As host cells capable of stably and continuously cloning and expressing the vector of the present invention, any host cells that are known in the art may be used, for example, and examples of the host cells include *E. coli* strains, such as *E. coli* Origami2, *E. coli* JM109, *E. coli* BL21 (DE3), *E. coli* RR1, *E. coli* LE392, *E. coli* B, *E. coli* X 1776, and *E. coli* W3110, *Bacillus* spp. strains, such as *Bacillus subtilis* and *Bacillus thuringiensis*, and Enterobacteriaceae strains, such as *Salmonella typhimurium, Serratia marcescens*, and various *Pseudomonas* spp.

In addition, in cases where the vector of the present invention is transformed into eukaryotic cells, yeast (*Saccharomyces cerevisiae*), insect cells, and animal cells (e.g., Chinese hamster ovary (CHO) cell lines, and W138, BHK, COS-7, 293, HepG2, 3T3, RIN, and MDCK cell lines) may be used as host cells.

According to an embodiment of the present invention, HEK293F cells are used as host cells transformed by the vector of the present invention.

When host cells are prokaryotic cells, the vector of the present invention may be delivered into the host cells by $CaCl_2$) method (Cohen, S. N. et al., Proc. Natl. Acac. Sci. USA, 9:2110-2114 (1973)), Hanahan method (Cohen, S. N. et al., Proc. Natl. Acac. Sci. USA, 9:2110-2114 (1973); and Hanahan, D., J. Mol. Biol., 166:557-580 (1983)), electroporation (Dower, W. J. et al., Nucleic. Acids Res., 16:6127-6145 (1988)), and the like. In addition, when host cells are eukaryotic cells, the vector may be injected into the host cells by microinjection (Capecchi, M. R., Cell, 22: 479 (1980), calcium phosphate precipitation (Graham, F. L. et al., Virology, 52: 456 (1973)), electroporation (Neumann, E. et al., EMBO J., 1: 841 (1982)), liposome-mediated transfection (Wong, T. K. et al., Gene, 10: 87 (1980)), DEAE-dextran treatment (Gopal, Mol. Cell Biol., 5:1188-1190 (1985)), gene bombardment (Yang et al., Proc. Natl. Acad. Sci., 87:9568-9572 (1990)), and the like.

Herein, the recombinant vector injected into the host cells can express the recombined polypeptide or polypeptide complex in the host cells, and in such a case, a large amount of polypeptides or polypeptide complexes are obtained. For example, when the vector contains a lac promoter, gene expression can be induced by treatment of host cells with IPTG.

The transformed host cells may be cultured by a known host cell culture method or a modified method thereof. For example, when the host cells are *E. coli*, a medium for culturing transgenic host cells may employ a natural medium or a synthetic medium so long as such a medium contains a carbon source, a nitrogen source, an inorganic salt, and the like, that can be efficiently used by *E. coli*. The usable carbon source includes: carbohydrates, such as glucose, fructose, and sucrose; starch, hydrolysates of starch; organic acids, such as acetic acid and propionic acid; and alcohols, such as ethanol, propanol, and glycerol. The nitrogen source includes: ammonia; ammonium salts of inorganic acids or organic acids, such as ammonium sulfate, ammonium acetate, and ammonium phosphate; peptone, meat extracts, yeast extracts, corn steep liquid, casein hydrolysates, soybean extracts, soybean hydrolysates; and various fermented cells and lysates thereof. The inorganic salt includes potassium dihydrogen phosphate, dipotassium hydrogen phosphate, magnesium phosphate, magnesium sulphate, sodium chloride, manganese sulphate, copper sulphate, calcium carbonate, and the like.

The culturing is usually carried out under aerobic conditions by, for example, a shaking culture or a rotation by a rotator. The culturing temperature is preferably in a range of 10-40° C., and the culturing time is generally for 5 hours to 7 days. The pH of the medium is preferably maintained at 3.0-9.0 during culturing. The pH of the medium can be adjusted by an inorganic or organic acid, an alkali solution, urea, calcium carbonate, ammonia, or the like. For maintenance and expression of recombinant vectors, if necessary, antibiotics, such as ampicillin, streptomycin, chloramphenicol, kanamycin, and tetracycline, may be added during culturing. When host cells transformed by a recombinant expression vector having an inducible promoter is cultured, an inducer suitable for a medium may be added if necessary. For example, isopropyl-3-D-thiogalactopyranoside (IPTG) may be added when the expression vector contains a lac promoter, and indoleacrylic acid may be added when the expression vector contains a trp promoter.

Advantageous Effects

Features and advantages of the present invention are summarized as follows.

(a) The present invention provides a polypeptide (Affibody molecule) improved in protein purity and affinity for IL-6 through the prevention of glycosylation even when produced in eukaryotic cells.

(b) The present invention provides a polypeptide complex improved in protein purity and affinity for IL-6 by containing the polypeptide (Affibody molecule) and an antibody or an antigen-binding fragment thereof specifically binding to any target antigen.

(c) The present invention provides respective methods for manufacturing the polypeptide (Affibody molecule) and the polypeptide complex composed of an antibody and antigen-binding fragment thereof.

The polypeptide or the complex thereof of the present invention, even when produced in eukaryotic cells, causes no glycosylation, leading to high purity in the produced protein and high affinity for a target antigen, and thus the polypeptide or the complex thereof of the present invention is highly valuable as a reagent for diagnosis or treatment of a disease.

BRIEF DESCRIPTION OF THE DRAWINGS

FIGS. 7A and 7B show $EC_{50}$ values of the polypeptide complexes (bispecific antibodies) of the present invention to target antigens (TNF-α and IL-6).

In FIGS. 2 to 7 and the present specification, NL5 refers to the bispecific antibody in which the Affibody sequence was linked to the N-terminus of the light chain of the adalimumab antibody via a linker consisting of five amino acids (GGGGS); CL5 refers to the bispecific antibody in which the Affibody sequence was linked to the C-terminus of the light chain of the adalimumab antibody via a linker consisting of five amino acids (GGGGS); and NH5 refers to the bispecific antibody in which the Affibody sequence was linked to the N-terminus of the heavy chain of the adalimumab antibody via a linker consisting of five amino acids (GGGGS).

DETAILED DESCRIPTION

Hereinafter, the present invention will be described in more detail with reference to examples. These examples are only for illustrating the present invention more specifically, and it will be apparent to those skilled in the art that the scope of the present invention is not limited by these examples.

EXAMPLES

Example 1: Glycosylation Occurring in Affibody Protein Upon Expression in Animal Cells As bispecific antibodies, in which the Affibody protein consisting of the amino acid sequence of SEQ ID NO: 1 and specifically binding to IL-6 is genetically linked with an antibody to TNF (adalimumab; containing the heavy chain of SEQ ID NO: 5 and the light chain of SEQ ID NO: 6), were produced in animal cells (HEK293F cells), glycosylation occurs, and as a result, the molecular weights of the bispecific antibody proteins were not constant and several bands were shown (see Lane 1 parent in FIGS. 2 to 4). As a result of analyzing the primary sequence of the Affibody protein consisting of the amino acid sequence of SEQ ID NO: 1, the possibility of glycosylation was predicted on asparagine (Asn, N) at the 21st and 52nd amino acid positions (Eisenhaber B & Eisenhaber F, 2010, Methods Mol Biol.).

Next, in order to investigate whether glycosylation observed in the Affibody molecule and adalimumab antibody-linked substance occurred on the Affibody protein, the present inventors developed variants resulting from mutation of the predicted glycosylation sites.

TABLE 1

| Primers | Nucleotide sequence (5'→3') |
|---|---|
| CMV forward | CGCAAATGGGCGGTAGGCGTG (SEQ ID NO: 9) |
| TK poly reverse | CTTCCGTGTTTCAGTTAGC (SEQ ID NO: 10) |

TABLE 1-continued

| Primers | Nucleotide sequence (5'→3') |
|---|---|
| T23N-F | GTTACCTAACTTAAACATTGAGCAAATG (SEQ ID NO: 11) |
| T23N-R | CATTTGCTCAATGTTTAAGTTAGGTAAC (SEQ ID NO: 12) |
| S54A-F | AAGCTAAATGATGCCCAGGCGCCGAAA (SEQ ID NO: 13) |
| S54A-R | TTTCGGCGCCTGGGCATCATTTAGCTT (SEQ ID NO: 14) |

In order to remove the possibility of glycosylation in the Affibody sequence, variants, in which threonine (T) is substituted with asparagine (N) at position 23 and serine(S) is substituted with alanine (A) at position 54, were manufactured by overlapping PCR using the PCR primers on Table 1. Through this, three types of bispecific antibody variants (SM1, SM2, and DM1) were manufactured as below.

Figure 1:
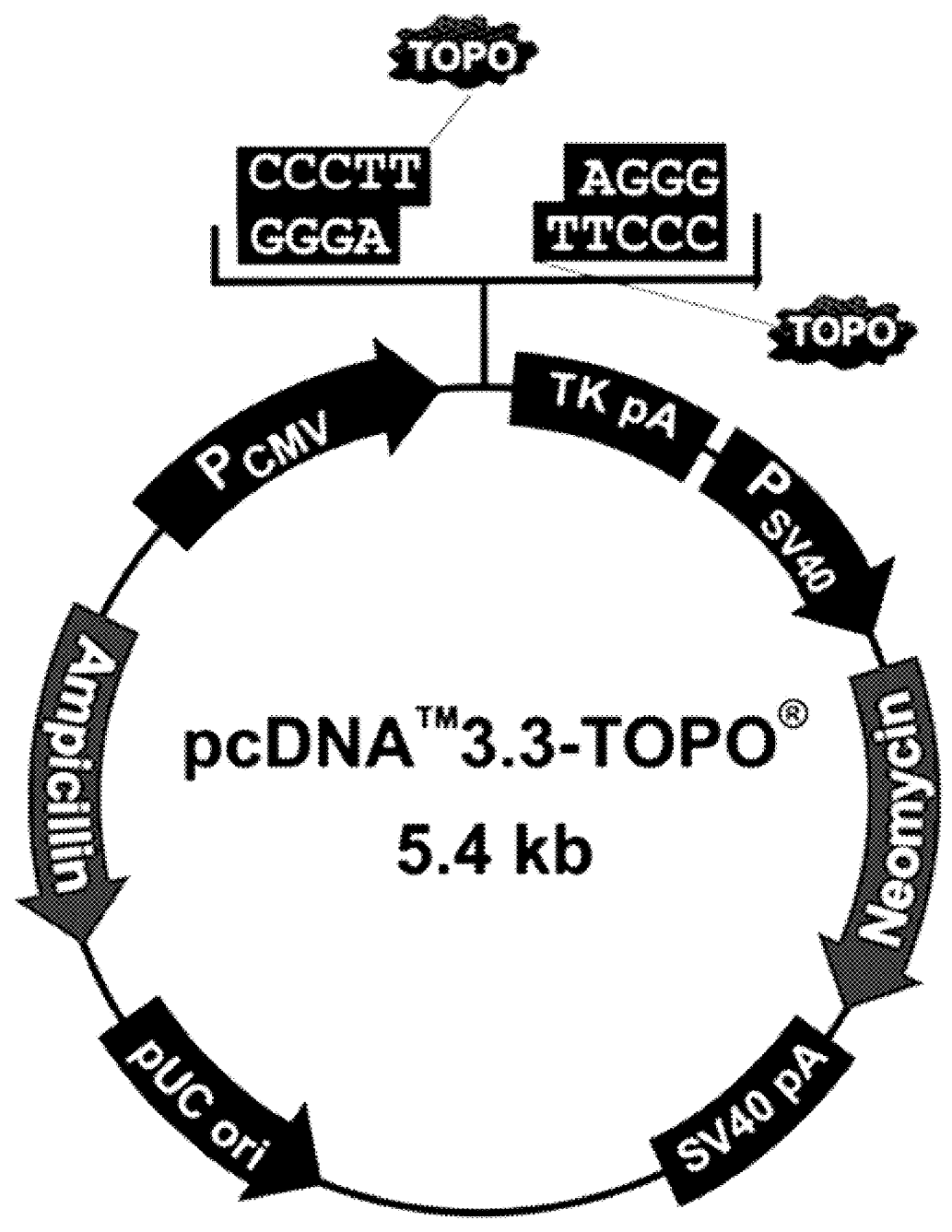
FIG. 1 shows a vector map of the expression vector (pcDNA3.3 vector, Invitrogen, cat. #. K8300-01) used to induce mutation so as to prevent the occurrence of glycosylation in the present invention.

For single mutagenesis, parent DNA obtained by inserting an anti-human TNF-α and IL-6 bispecific antibody into the pcDNA3.3 vector (Invitrogen, cat. #. K8300-01) in FIG. 1 was used, and overlapping PCR was performed under the following conditions.

First, mutation was induced to substitute threonine with asparagine at the 23rd amino acid position. For the production of the N-terminal DNA fragment on the basis of threonine at the 23rd amino acid position to be mutated, 50 ng of template DNA, 4 μL of each of 10 pmol/μL CMV forward primer and T23N-R primer, and 10 μL of 10×pfu polymerase mixture (ELPIS biotech, EBT-1011) were placed in PCR tube, and then distilled water was added to a total reaction volume of 50 μL. Thereafter, PCR reaction was performed.

In addition, the C-terminal DNA fragment on the basis of threonine at the 23rd amino acid position to be mutated was produced using T23N-F and TK poly reverse primers under the conditions as above.

The two DNA fragments produced from PCR reaction were loaded on agarose gel, and then separated from the agarose gel by using the DNA gel elution kit (iNtRON BIOTECHNOLOGY, cat. #. 17288). Thereafter, 50 ng of each of the two separated DNA fragments used as template DNA, 4 μL of each of 10 pmol/μL CMV forward and TK poly reverse primers, and 10 μL of 10×pfu polymerase mixture (ELPIS, cat. #. EBT-1011) were placed in PCR tube, and then distilled water was added to a total reaction volume of 50 μL. Thereafter, overlapping PCR for linking the two DNA fragments was performed to fabricate a variant sequence in which threonine was substituted with arginine at position 23.

Then, mutation was induced to substitute serine with alanine at the 54th amino acid position. Overlapping PCR was performed by the same method as when the 23rd amino acid was substituted, except that S54A-F and S54A-R were used instead of T23N-F and T23N-R, as primers. The overlapping PCR product was subjected to DNA clean-up using the gel elution kit.

Last, double mutation was induced to substitute both of the amino acids at positions 23 and 54. Such double mutagenesis was carried out by substituting the amino acid at position 23 in the 53rd amino acid-substituted DNA used as a template.

The purified bispecific DNA and the pcDNA3.3 vector were double digested by ClaI (NEB, cat. #. R0197L) and XhoI (NEB, cat. #. R0146L), respectively, and then ligated.

Three types of Affibody sequences, which are bispecific antibody variants thus obtained, binding to both of TNF-α and IL-6, are shown in Table 2.

TABLE 2

| Affibody | Amino acid sequence | Comment |
|---|---|---|
| Parent<br>SEQ ID NO: 1 | AEAKYAKEEQ RAWREIHLLP<br>NLTIEQMAAF IWKLLDDPSQ<br>S̲SELLSEAKK LNDSQAPK | Under bar:<br>Predicted<br>glycosylation<br>site |
| SM1<br>SEQ ID NO: 2 | AEAKYAKEEQ RAWREIHLLP<br>NLNIEQMAAF IWKLLDDPSQ<br>SS̲ELLSEAKK LNDSQAPK | Under bar:<br>Substituted<br>amino acid |
| SM2<br>SEQ ID NO: 3 | AEAKYAKEEQ RAWREIHLLP<br>NLTIEQMAAF IWKLLDDPSQ<br>SSELLSEAKK LNDAQAPK | |
| DM1<br>SEQ ID NO: 4 | AEAKYAKEEQ RAWREIHLLP<br>NLNIEQMAAF IWKLLDDPSQ<br>SS̲ELLSEAKK LNDAQAPK | |

As shown in Table 2, the single mutation sequence in which threonine was substituted with asparagine at the 23rd amino acid position in the Affibody sequence, and the single mutation sequence in which serine was substituted with alanine at the 54th amino acid position in the Affibody sequence were named SM1 and SM2, respectively, and the double mutation sequence in which both of the 23rd and 54rd amino acids were substituted was named DM1. Therefore, these sequences were used for studies of expression of bispecific antibodies in animal cells and characterization thereof.

Example 2: Production of Three Types of Bispecific Antibody Variants by Using Animal Cells The three types of bispecific antibody variants and the bispecific antibody of the parent sequence, manufactured in example 1, were produced using HEK293F cells.

First, HEK293F cells were grown to an amount of 100 mL at $1 \times 10^6$ cell/mL, and then was subjected to shaking incubation under conditions of 37° C., 8% $CO_2$, and RPM125.

Then, 5 mL of a culture medium was placed in a 15 mL-sterile tube, and heavy chain DNA and light chain DNA were added at a ratio of 1:2, followed by good mixing, to prepare DNA. PEI (Polysciences, cat. #. 23966) was placed in the 15 mL-tube containing the culture medium and DNA, followed by good mixing, and then HEK293F cells were added, followed by culturing for 7 days.

The bispecific antibodies were purified from the culture liquid by using Protein A resin (GE healthcare, cat. #. 17-5438-03), and the buffer was exchanged using diafiltration (Satorius, cat. #. VS2002). The purified bispecific antibodies were quantified by measurement of absorbance at a wavelength of 280 nm. The purified bispecific antibodies were analyzed on 12% SDS-PAGE.

Figure 2:
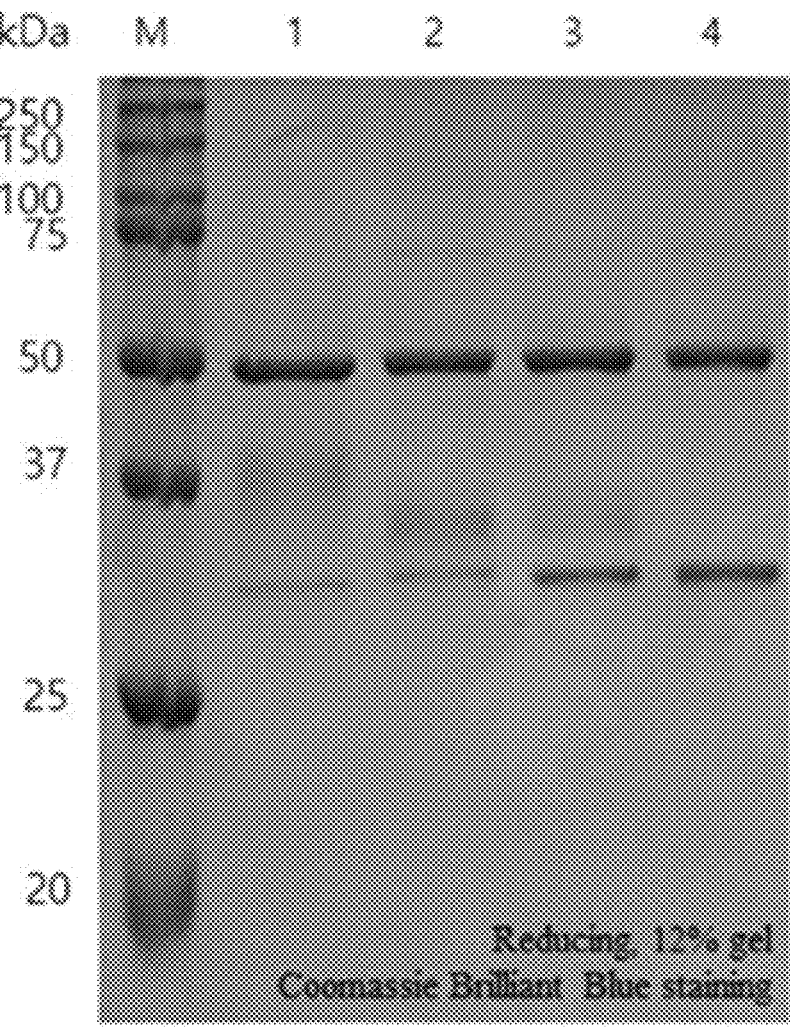
FIG. 2 shows purity of polypeptide complexes (bispecific antibodies) of the present invention, in which the polypeptides (Affibody molecules) having affinity for IL-6 were linked to the N-terminus of the light chain of an antibody.
Figure 4:
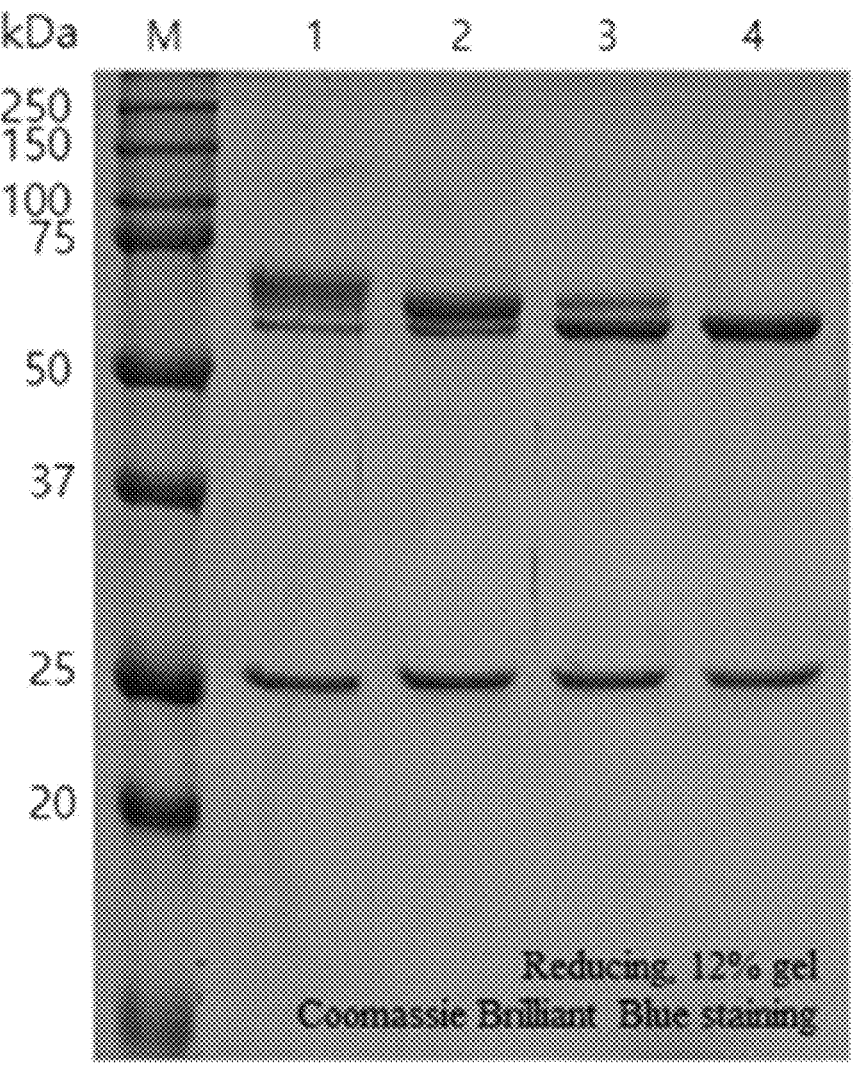
FIG. 4 shows purity of polypeptide complexes (bispecific antibodies) of the present invention, in which the polypeptides (Affibody molecules) having affinity for IL-6 were linked to the N-terminus of the heavy chain of an antibody.

From the comparison of the produced bispecific antibodies, Parent and three types of variants, glycosylation occurred on asparagine at both of positions 21 and 52 when the Affibody protein was linked to the N-terminus of the antibody, and no glycosylation occurred in only DM1 in which both of the two sites were mutated (FIGS. 2 and 4).

Figure 3:
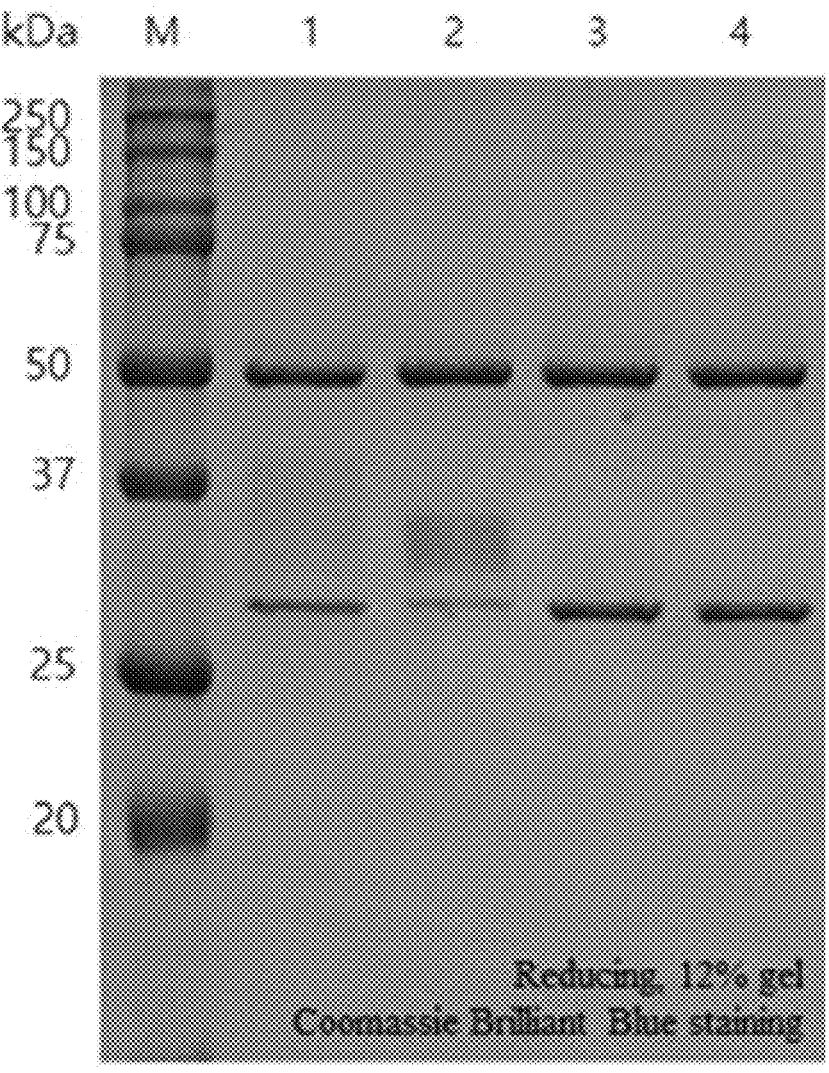
FIG. 3 shows purity of polypeptide complexes (bispecific antibodies) of the present invention, in which the polypeptides (Affibody molecules) having affinity for IL-6 were linked to the C-terminus of the light chain of an antibody.

When the Affibody protein was linked to the C-terminus of the antibody, glycosylation definitely occurred on asparagine at position 52, whereas very weak glycosylation occurred on asparagine at position 21 (FIG. 3).

It could be confirmed through the above results that when the IL-6 binding Affibody protein was produced using animal cells, glycosylation occurred on asparagine at positions 21 and 52 in the Affibody sequence, and protein purity was improved when the amino acids at positions 23 and 54 in the Affibody sequence were substituted with other amino acids (SM1, SM2, and DM2) (FIGS. 2 and 4).

Example 3: Confirmation of Reduction in Binding Strength of Bispecific Antibody Due to Glycosylation A change in binding strength of the Affibody protein to a target protein due to glycosylation was analyzed as below.

In order to investigate the binding strength of the bispecific antibodies (Parent and three types of variants) fabricated in Example 2 to TNF-α or IL-6 alone, the following experiment was performed.

First, TNF-α (R&D systems, cat. #. 210-TA-100/CF) at 0.2 (g/mL or IL-6 (R&D systems, cat. #. 206-IL-050/CF) at 1 μg/mL were dispensed with 30 μL per well in ELISA plates (Corning, cat. #. 3690), and immobilized by incubation at 4° C. for 15 hours or longer. After 15 hours, the ELISA plates were washed three times with 0.05% tween20 PBS, and the bispecific antibodies were serially diluted from 60 nM to 1/5 folds seven times, dispensed with 30 UL each, and then incubated at 25° C. for 1 hour. After washing of the ELISA plates three times, anti-human IgG Fc-HRP (ThermoFisher, cat. #. 31423) was diluted to 0.2 μg/mL, and then 30 μL each was dispensed, followed by incubation at 25° C. for 45 minutes. Then, the plates were washed three times with 100 μL of 0.05% tween20 PBS. Last, the development was induced by addition of TMB (SurModics, cat. #. TMBC-1000-01). After 3 minutes, the development was stopped by addition of 1 N sulfuric acid (DUKSAN, cat. #. B8C411) to the plates for investigating the binding strength to TNF-α, and the absorbance was measured at 450 nm. After 5 minutes, the development was stopped by addition of 1 N sulfuric acid to the plates for investigating the binding strength to IL-6, and the absorbance was measured at 450 nm.

In order to investigate the double binding strength of the bispecific antibodies (Parent and three types of variants) fabricated in Example 2 to TNF-α and IL-6, the following experiment was performed.

First, TNF-α was immobilized at 0.2 μg/mL in ELISA plates, and treated with bispecific antibodies, and then treated with biotin-fused IL-6 at 0.1 μg/mL. Thereafter, avidin-HRP (Pierce, cat. #. 29994) was diluted to 0.2 ug/mL, and then 30 μL each was dispensed, followed by incubation. After incubation at 25° C. for 45 minutes, the plates were washed three times with 100 μL of 0.05% tween20 PBS, and then developed.

The results are shown in FIGS. 5 and 6.

Figure 5A:
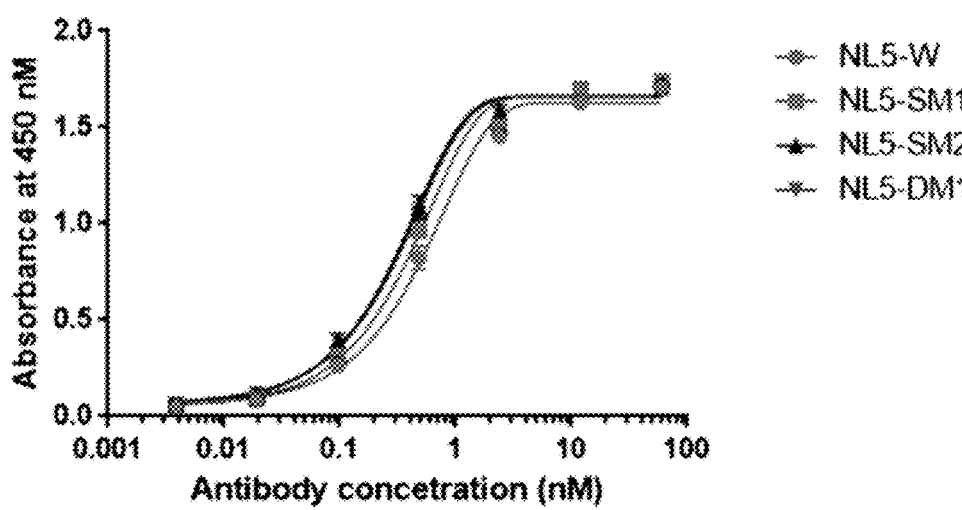
FIGS. 5A, 5B and 5C show binding ability of the polypeptide complexes (bispecific antibodies) of the present invention to target antigens (TNF-α and IL-6), the polypeptide complexes having the polypeptides (Affibody molecules) having affinity for IL-6 linked to the N-terminus of the light chain of an antibody.
Figure 5B:
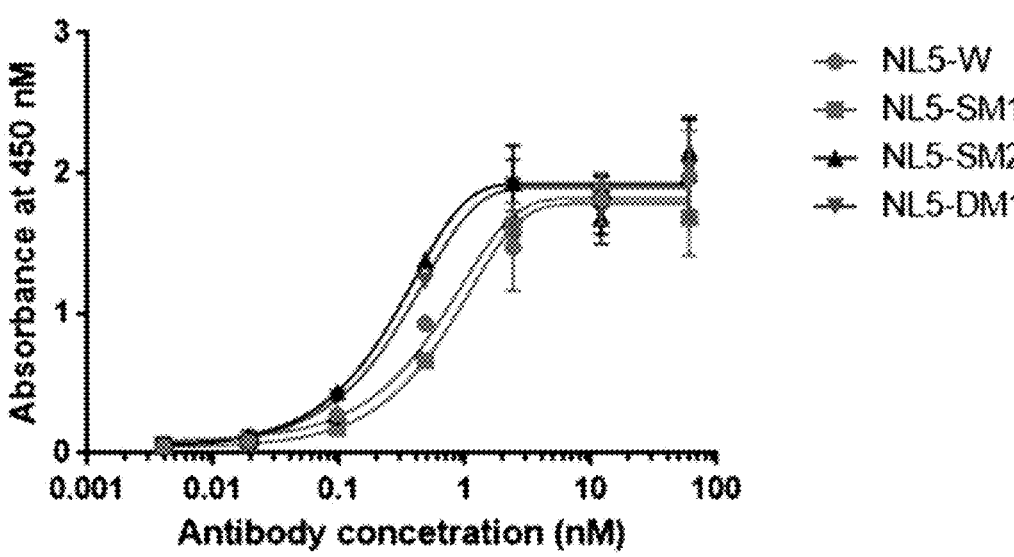
Figure 5C:
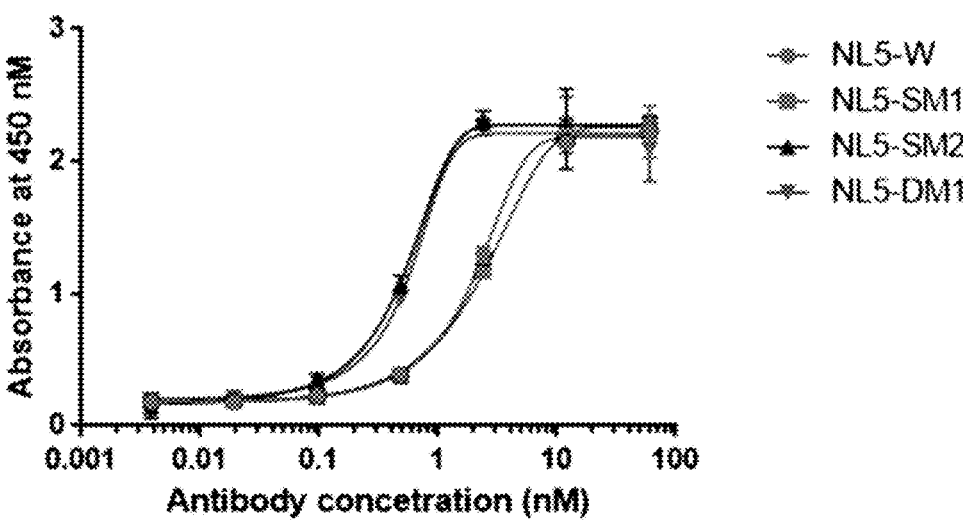
Figure 6A:
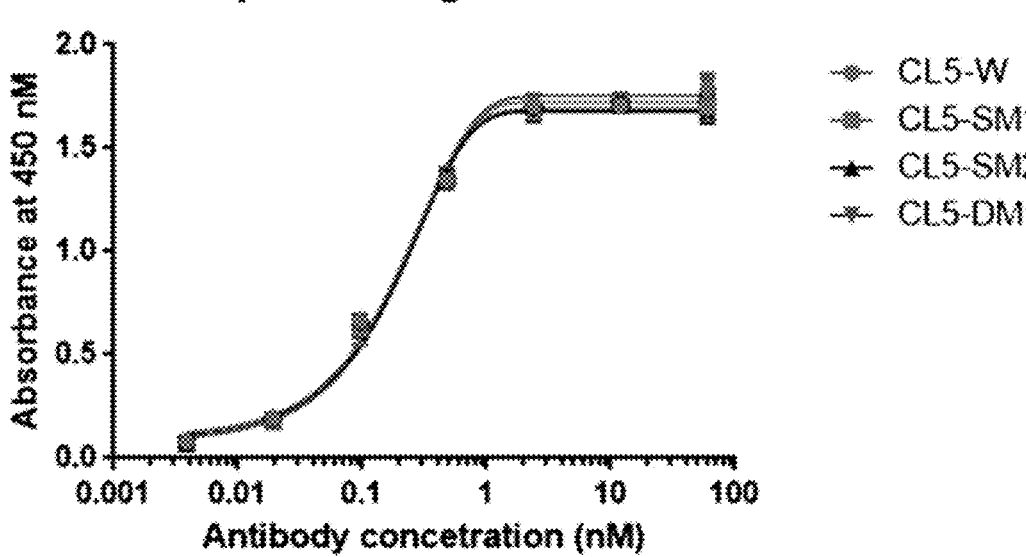
FIGS. 6A, 6B and 6C show binding ability of the polypeptide complexes (bispecific antibodies) of the present invention to target antigens (TNF-α and IL-6), the polypeptide complexes having the polypeptides (Affibody molecules) having affinity for IL-6 linked to the C-terminus of the light chain of an antibody.
Figure 6B:
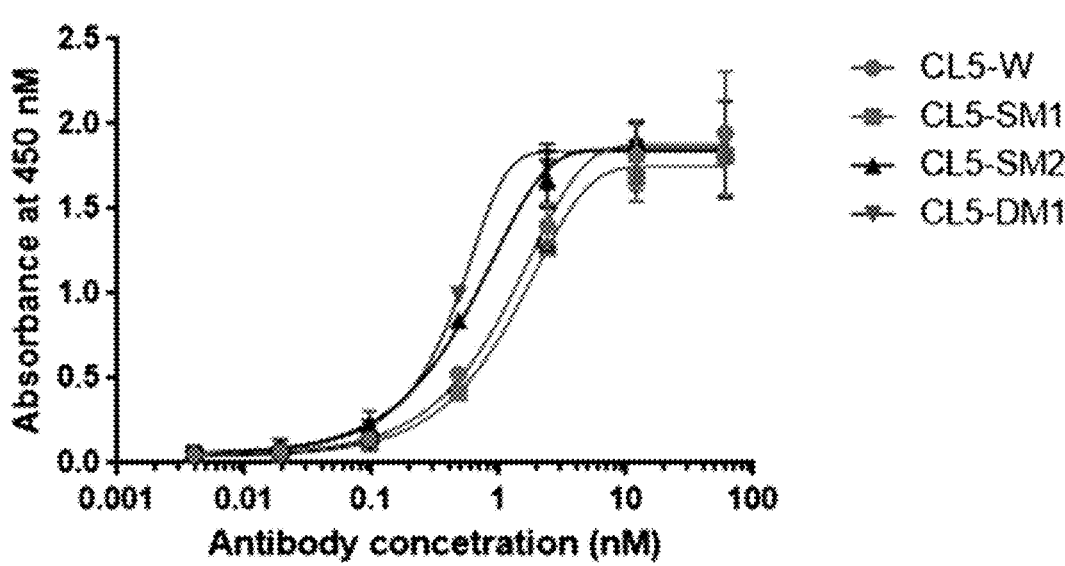
Figure 6C:
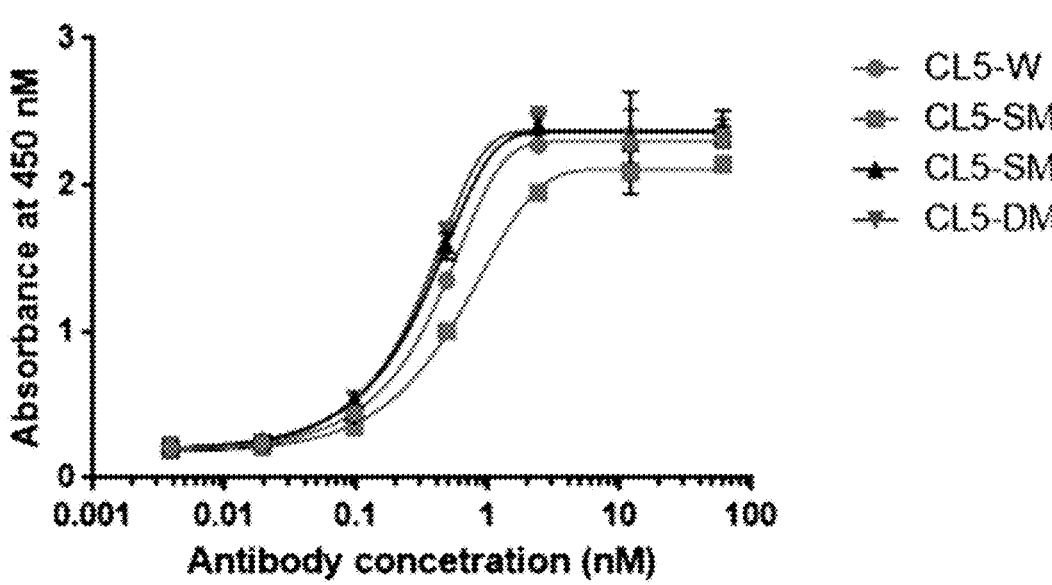

As a result of confirming binding strength, the binding strength of the adalimumab antibody to TNF-α did not change (FIGS. 5A and 6A). However, as for the binding strength of the Affibody molecules to IL-6, the binding strength of SM2 and DM1 was increased compared with the binding strength of Parent and SM1 (FIGS. 5B and 6B). As for the double binding strength to TNF-α and IL-6, the binding strength of SM2 and DM1 was increased compared with Parent and SM1 (FIGS. 5C and 6C).

It was confirmed from the results that the binding strength of the Affibody molecules was reduced by glycosylation on the amino acids at positions 21 and 52, and was increased by glycosylation prevention through mutation of the amino acids at positions 23 and 54.

The $EC_{50}$ values of the bispecific antibodies were measured using the software called GraphPad Prism6. A graph with respect to the O.D value over the antibody concentration was created in the form of four parameters by using ELISA experiments confirming the binding strength of the bispecific antibodies to TNF-α or IL-6 alone and ELISA experiment data confirming the double binding strength to TNF-α and IL-6, and then the $EC_{50}$ values were calculated.

The results are shown in FIGS. 7A and 7B.

As for the $EC_{50}$ value for IL-6, the values of SM2 and DM1 were lower compared with the values of Parent and SM1, and as for the $EC_{50}$ value for TNF-α and IL-6, the values of SM2 and DM1 were lower compared with the values of Parent and SM1. The above results quantitatively confirmed that the binding strength of the Affibody sequences was enhanced when threonine (T) was substituted with asparagine (N) at the 23rd amino acid reside position and serine(S) was substituted with alanine (A) at the 54th amino acid residue position in the Affibody sequence of the present invention (see FIG. 7).

This application contains references to amino acid sequences and/or nucleic acid sequences which have been submitted concurrently herewith as the sequence listing text file entitled "000162usnp_2ndAmendedSequenceListing.TXT", file size 15 KiloBytes (KB), created on 1 Nov. 2021. The aforementioned sequence listing is hereby incorporated by reference in its entirety pursuant to 37 C.F.R. § 1.52(e)(5)."

---

What is claimed is:

1. A polypeptide consisting of an amino acid sequence selected from the group consisting of SEQ ID NOs: 2, 3, and 4.

2. A polypeptide complex comprising:
   i) the polypeptide of claim 1; and
   ii) an antibody or an antigen-binding fragment thereof that specifically binds to a target antigen,
   wherein i) and ii) are linked to each other.

3. The polypeptide complex of claim 2, wherein the target antigen of ii) the antibody or the antigen-binding fragment thereof is selected from the group consisting of angiogenin 2 (Ang-2), vascular endothelial growth factor, tumor necrosis factor, TNF-α, TNFSF11, TNFSF13, TNFSF13B, TNFSF14, TNFSF15, insulin-like growth factor, interleukin 1α, interleukin 1β, interleukin 10, interleukin 17A, interleukin 12, interleukin 23, interleukin 33, granulocyte mac-rophage colony-stimulating factor, granulocyte colony stimulating factor, high-mobility group protein B1, lipopo-lysaccharide, toll-like receptor 4, nerve growth factor, chemokine C-C motif ligand 19, chemokine C-C motif ligand 21, chemokine C-C motif ligand 4, and interferon alpha.

4. The polypeptide complex of claim 2, wherein the target antigen of ii) the antibody or the antigen-binding fragment thereof is tumor necrosis factor-α (TNF-α).

5. The polypeptide complex of claim 2, wherein in ii), the antibody or the antigen-binding fragment thereof is selected from the group consisting of adalimumab, infliximab, goli-mumab, and certolizumab pegol, and antigen-binding frag-ments thereof.

6. The polypeptide complex of claim 2, wherein in ii), the antibody or the antigen-binding fragment thereof comprises the amino acid sequence of SEQ ID NO: 5.

7. The polypeptide complex of claim 2, wherein i) the polypeptide and ii) the antibody or the antigen-binding fragment thereof are linked to each other via at least one linker.

8. The polypeptide complex of claim 7, wherein the linker consists of an amino acid sequence represented by the general formula (GnSm)p or (SmGn)p, wherein n, m, and p each are independent;

n is an integer of 1 to 7;

m is an integer of 0 to 7;

the sum of n and m is an integer of 8 or less; and p is an integer of 1 to 7.

9. A nucleic acid consisting of a nucleotide sequence encoding the polypeptide of claim 1.

10. A nucleic acid consisting of a nucleotide sequence encoding the polypeptide complex of claim 2.

\* \* \* \* \*

SEQUENCE LISTING

```
<160> NUMBER OF SEQ ID NOS: 18

<210> SEQ ID NO 1
<211> LENGTH: 58
<212> TYPE: PRT
<213> ORGANISM: Artificial Sequence
<220> FEATURE:
<223> OTHER INFORMATION: IL-6 binding polypeptide

<400> SEQUENCE: 1

Ala Glu Ala Lys Tyr Ala Lys Glu Glu Gln Arg Ala Trp Arg Glu Ile
1               5                   10                  15

His Leu Leu Pro Asn Leu Thr Ile Glu Gln Met Ala Ala Phe Ile Trp
            20                  25                  30

Lys Leu Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: IL-6 binding polypeptide with improved purity
      and affinity (SM1)

<400> SEQUENCE: 2

Ala Glu Ala Lys Tyr Ala Lys Glu Glu Gln Arg Ala Trp Arg Glu Ile
1               5                   10                  15

His Leu Leu Pro Asn Leu Asn Ile Glu Gln Met Ala Ala Phe Ile Trp
            20                  25                  30

Lys Leu Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 3
<211> LENGTH: 58
<212> TYPE: PRT
<213> ORGANISM: Artificial Sequence
<220> FEATURE:
<223> OTHER INFORMATION: IL-6 binding polypeptide with improved purity
      and affinity (SM2)

<400> SEQUENCE: 3
```

-continued

```
Ala Glu Ala Lys Tyr Ala Lys Glu Glu Gln Arg Ala Trp Arg Glu Ile
1               5                   10                  15

His Leu Leu Pro Asn Leu Thr Ile Glu Gln Met Ala Ala Phe Ile Trp
            20                  25                  30

Lys Leu Leu Asp Asp Pro Ser Gln Ser Ser Glu Leu Leu Ser Glu Ala
        35                  40                  45

Lys Lys Leu Asn Asp Ala Gln Ala Pro Lys
        50                  55

<210> SEQ ID NO 4
<211> LENGTH: 58
<212> TYPE: PRT
<213> ORGANISM: Artificial Sequence
<220> FEATURE:
<223> OTHER INFORMATION: IL-6 binding polypeptide with improved purity
      and affinity (DM1)

<400> SEQUENCE: 4

Ala Glu Ala Lys Tyr Ala Lys Glu Glu Gln Arg Ala Trp Arg Glu Ile
1               5                   10                  15

His Leu Leu Pro Asn Leu Asn Ile Glu Gln Met Ala Ala Phe Ile Trp
            20                  25                  30

Lys Leu Leu Asp Asp Pro Ser Gln Ser Ser Glu Leu Leu Ser Glu Ala
        35                  40                  45

Lys Lys Leu Asn Asp Ala Gln Ala Pro Lys
        50                  55

<210> SEQ ID NO 5
<211> LENGTH: 451
<212> TYPE: PRT
<213> ORGANISM: Artificial Sequence
<220> FEATURE:
<223> OTHER INFORMATION: Adalimumab heavy chain

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

-continued

```
                180                   185                   190
Pro Ser Ser Ser Leu Gly Thr Gln Thr Tyr Ile Cys Asn Val Asn His
        195                   200                   205
Lys Pro Ser Asn Thr Lys Val Asp Lys Lys Val Glu Pro Lys Ser Cys
    210                   215                   220
Asp Lys Thr His Thr Cys Pro Pro Cys Pro Ala Pro Glu Leu Leu Gly
225                   230                   235                   240
Gly Pro Ser Val Phe Leu Phe Pro Pro Lys Pro Lys Asp Thr Leu Met
                245                   250                   255
Ile Ser Arg Thr Pro Glu Val Thr Cys Val Val Val Asp Val Ser His
                260                   265                   270
Glu Asp Pro Glu Val Lys Phe Asn Trp Tyr Val Asp Gly Val Glu Val
        275                   280                   285
His Asn Ala Lys Thr Lys Pro Arg Glu Glu Gln Tyr Asn Ser Thr Tyr
        290                   295                   300
Arg Val Val Ser Val Leu Thr Val Leu His Gln Asp Trp Leu Asn Gly
305                   310                   315                   320
Lys Glu Tyr Lys Cys Lys Val Ser Asn Lys Ala Leu Pro Ala Pro Ile
                325                   330                   335
Glu Lys Thr Ile Ser Lys Ala Lys Gly Gln Pro Arg Glu Pro Gln Val
            340                   345                   350
Tyr Thr Leu Pro Pro Ser Arg Asp Glu Leu Thr Lys Asn Gln Val Ser
        355                   360                   365
Leu Thr Cys Leu Val Lys Gly Phe Tyr Pro Ser Asp Ile Ala Val Glu
    370                   375                   380
Trp Glu Ser Asn Gly Gln Pro Glu Asn Asn Tyr Lys Thr Thr Pro Pro
385                   390                   395                   400
Val Leu Asp Ser Asp Gly Ser Phe Phe Leu Tyr Ser Lys Leu Thr Val
                405                   410                   415
Asp Lys Ser Arg Trp Gln Gln Gly Asn Val Phe Ser Cys Ser Val Met
            420                   425                   430
His Glu Ala Leu His Asn His Tyr Thr Gln Lys Ser Leu Ser Leu Ser
        435                   440                   445
Pro Gly Lys
    450
```

```
<210> SEQ ID NO 6
<211> LENGTH: 214
<212> TYPE: PRT
<213> ORGANISM: Artificial Sequence
<220> FEATURE:
<223> OTHER INFORMATION: Adalimumab light chain

<400> SEQUENCE: 6

Asp Ile Gln Met Thr Gln Ser Pro Ser Ser Leu Ser Ala Ser Val Gly
1                   5                   10                  15
Asp Arg Val Thr Ile Thr Cys Arg Ala Ser Gln Gly Ile Arg Asn Tyr
            20                  25                  30
Leu Ala Trp Tyr Gln Gln Lys Pro Gly Lys Ala Pro Lys Leu Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Arg Tyr Asn Arg Ala Pro Tyr
```

-continued

```
                    85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

```
<210> SEQ ID NO 7
<211> LENGTH: 58
<212> TYPE: PRT
<213> ORGANISM: Artificial Sequence
<220> FEATURE:
<223> OTHER INFORMATION: General Formula 1
<220> FEATURE:
<221> NAME/KEY: MISC_FEATURE
<222> LOCATION: (3)..(3)
<223> OTHER INFORMATION: Xaa can be any amino acid residue
<220> FEATURE:
<221> NAME/KEY: MISC_FEATURE
<222> LOCATION: (5)..(5)
<223> OTHER INFORMATION: Xaa can be any amino acid residue
<220> FEATURE:
<221> NAME/KEY: MISC_FEATURE
<222> LOCATION: (6)..(6)
<223> OTHER INFORMATION: Xaa can be any amino acid residue
<220> FEATURE:
<221> NAME/KEY: MISC_FEATURE
<222> LOCATION: (9)..(9)
<223> OTHER INFORMATION: Xaa can be any amino acid residue
<220> FEATURE:
<221> NAME/KEY: MISC_FEATURE
<222> LOCATION: (10)..(10)
<223> OTHER INFORMATION: Xaa can be any amino acid residue
<220> FEATURE:
<221> NAME/KEY: MISC_FEATURE
<222> LOCATION: (11)..(11)
<223> OTHER INFORMATION: Xaa can be any amino acid residue
<220> FEATURE:
<221> NAME/KEY: MISC_FEATURE
<222> LOCATION: (13)..(13)
<223> OTHER INFORMATION: Xaa can be any amino acid residue
<220> FEATURE:
<221> NAME/KEY: MISC_FEATURE
<222> LOCATION: (14)..(14)
<223> OTHER INFORMATION: Xaa can be any amino acid residue
<220> FEATURE:
<221> NAME/KEY: MISC_FEATURE
<222> LOCATION: (17)..(17)
<223> OTHER INFORMATION: Xaa can be any amino acid residue
<220> FEATURE:
<221> NAME/KEY: MISC_FEATURE
<222> LOCATION: (18)..(18)
<223> OTHER INFORMATION: Xaa can be any amino acid residue
<220> FEATURE:
<221> NAME/KEY: MISC_FEATURE
<222> LOCATION: (24)..(24)
<223> OTHER INFORMATION: Xaa can be any amino acid residue
<220> FEATURE:
<221> NAME/KEY: MISC_FEATURE
```

```
<222> LOCATION: (25)..(25)
<223> OTHER INFORMATION: Xaa can be any amino acid residue
<220> FEATURE:
<221> NAME/KEY: MISC_FEATURE
<222> LOCATION: (27)..(27)
<223> OTHER INFORMATION: Xaa can be any amino acid residue
<220> FEATURE:
<221> NAME/KEY: MISC_FEATURE
<222> LOCATION: (28)..(28)
<223> OTHER INFORMATION: Xaa can be any amino acid residue
<220> FEATURE:
<221> NAME/KEY: MISC_FEATURE
<222> LOCATION: (32)..(32)
<223> OTHER INFORMATION: Xaa can be any amino acid residue
<220> FEATURE:
<221> NAME/KEY: MISC_FEATURE
<222> LOCATION: (33)..(33)
<223> OTHER INFORMATION: Xaa can be any amino acid residue
<220> FEATURE:
<221> NAME/KEY: MISC_FEATURE
<222> LOCATION: (35)..(35)
<223> OTHER INFORMATION: Xaa can be any amino acid residue
<220> FEATURE:
<221> NAME/KEY: MISC_FEATURE
<222> LOCATION: (42)..(42)
<223> OTHER INFORMATION: Xaa can be any amino acid residue
<220> FEATURE:
<221> NAME/KEY: MISC_FEATURE
<222> LOCATION: (43)..(43)
<223> OTHER INFORMATION: Xaa can be any amino acid residue
<220> FEATURE:
<221> NAME/KEY: MISC_FEATURE
<222> LOCATION: (46)..(46)
<223> OTHER INFORMATION: Xaa can be any amino acid residue

<400> SEQUENCE: 7

Val Asp Xaa Lys Xaa Xaa Lys Glu Xaa Xaa Xaa Ala Xaa Xaa Glu Ile
1               5                   10                  15

Xaa Xaa Leu Pro Asn Leu Thr Xaa Xaa Gln Xaa Xaa Ala Phe Ile Xaa
            20                  25                  30

Xaa Leu Xaa Asp Asp Pro Ser Gln Ser Xaa Xaa Leu Leu Xaa Glu Ala
        35                  40                  45

Lys Lys Leu Asn Asp Ser Gln Ala Pro Lys
    50                  55

<210> SEQ ID NO 8
<211> LENGTH: 55
<212> TYPE: PRT
<213> ORGANISM: Artificial Sequence
<220> FEATURE:
<223> OTHER INFORMATION: General Formula 2
<220> FEATURE:
<221> NAME/KEY: MISC_FEATURE
<222> LOCATION: (9)..(9)
<223> OTHER INFORMATION: Xaa can be any amino acid residue
<220> FEATURE:
<221> NAME/KEY: MISC_FEATURE
<222> LOCATION: (10)..(10)
<223> OTHER INFORMATION: Xaa can be any amino acid residue
<220> FEATURE:
<221> NAME/KEY: MISC_FEATURE
<222> LOCATION: (11)..(11)
<223> OTHER INFORMATION: Xaa can be any amino acid residue
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: Xaa can be any amino acid residue
<220> FEATURE:
<221> NAME/KEY: MISC_FEATURE
<222> LOCATION: (18)..(18)
```

-continued

```
<223> OTHER INFORMATION: Xaa can be any amino acid residue
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa can be any amino acid residue
<220> FEATURE:
<221> NAME/KEY: MISC_FEATURE
<222> LOCATION: (25)..(25)
<223> OTHER INFORMATION: Xaa can be any amino acid residue
<220> FEATURE:
<221> NAME/KEY: MISC_FEATURE
<222> LOCATION: (27)..(27)
<223> OTHER INFORMATION: Xaa can be any amino acid residue
<220> FEATURE:
<221> NAME/KEY: MISC_FEATURE
<222> LOCATION: (28)..(28)
<223> OTHER INFORMATION: Xaa can be any amino acid residue
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: MISC_FEATURE
<222> LOCATION: (32)..(32)
<223> OTHER INFORMATION: Xaa can be any amino acid residue
<220> FEATURE:
<221> NAME/KEY: MISC_FEATURE
<222> LOCATION: (33)..(33)
<223> OTHER INFORMATION: Xaa can be any amino acid residue
<220> FEATURE:
<221> NAME/KEY: MISC_FEATURE
<222> LOCATION: (35)..(35)
<223> OTHER INFORMATION: Xaa can be any amino acid residue
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: MISC_FEATURE
<222> LOCATION: (42)..(42)
<223> OTHER INFORMATION: Xaa can be any amino acid residue
<220> FEATURE:
<221> NAME/KEY: MISC_FEATURE
<222> LOCATION: (43)..(43)
<223> OTHER INFORMATION: Xaa can be any amino acid residue
<220> FEATURE:
<221> NAME/KEY: MISC_FEATURE
<222> LOCATION: (46)..(46)
<223> OTHER INFORMATION: Xaa can be any amino acid residue

<400> SEQUENCE: 8

Ala Glu Ala Lys Tyr Ala Lys Glu Xaa Xaa Xaa Ala Ile Xaa Xaa Leu
1               5                   10                  15

Pro Asn Leu Thr Xaa Xaa Gln Xaa Xaa Ala Phe Ile Xaa Xaa Leu Xaa
            20                  25                  30

Asp Asp Pro Ser Gln Ser Xaa Xaa Leu Leu Xaa Glu Ala Lys Lys Leu
        35                  40                  45

Asn Asp Ser Gln Ala Pro Lys
    50                  55

<210> SEQ ID NO 9
<211> LENGTH: 21
<212> TYPE: PRT
<213> ORGANISM: Artificial Sequence
<220> FEATURE:
<223> OTHER INFORMATION: CMV forward primer

<400> SEQUENCE: 9

Cys Gly Cys Ala Ala Ala Thr Gly Gly Gly Cys Gly Gly Thr Ala Gly
```

```
1               5               10              15

Gly Cys Gly Thr Gly
        20

<210> SEQ ID NO 10
<211> LENGTH: 19
<212> TYPE: PRT
<213> ORGANISM: Artificial Sequence
<220> FEATURE:
<223> OTHER INFORMATION: TK poly reverse primer

<400> SEQUENCE: 10

Cys Thr Thr Cys Cys Gly Thr Gly Thr Thr Thr Cys Ala Gly Thr Thr
1               5               10              15

Ala Gly Cys

<210> SEQ ID NO 11
<211> LENGTH: 28
<212> TYPE: PRT
<213> ORGANISM: Artificial Sequence
<220> FEATURE:
<223> OTHER INFORMATION: T23N-F primer

<400> SEQUENCE: 11

Gly Thr Thr Ala Cys Cys Thr Ala Ala Cys Thr Thr Ala Ala Ala Cys
1               5               10              15

Ala Thr Thr Gly Ala Gly Cys Ala Ala Ala Thr Gly
        20              25

<210> SEQ ID NO 12
<211> LENGTH: 28
<212> TYPE: PRT
<213> ORGANISM: Artificial Sequence
<220> FEATURE:
<223> OTHER INFORMATION: T23N-R primer

<400> SEQUENCE: 12

Cys Ala Thr Thr Thr Gly Cys Thr Cys Ala Ala Thr Gly Thr Thr Thr
1               5               10              15

Ala Ala Gly Thr Thr Ala Gly Gly Thr Ala Ala Cys
        20              25

<210> SEQ ID NO 13
<211> LENGTH: 27
<212> TYPE: PRT
<213> ORGANISM: Artificial Sequence
<220> FEATURE:
<223> OTHER INFORMATION: S54A-F primer

<400> SEQUENCE: 13

Ala Ala Gly Cys Thr Ala Ala Ala Thr Gly Ala Thr Gly Cys Cys Cys
1               5               10              15

Ala Gly Gly Cys Gly Cys Cys Gly Ala Ala Ala
        20                  25

<210> SEQ ID NO 14
<211> LENGTH: 27
<212> TYPE: PRT
<213> ORGANISM: Artificial Sequence
<220> FEATURE:
<223> OTHER INFORMATION: S54A-R primer

<400> SEQUENCE: 14

Thr Thr Thr Cys Gly Gly Cys Gly Cys Cys Thr Gly Gly Gly Cys Ala
```

-continued

```
1              5              10             15

Thr Cys Ala Thr Thr Thr Ala Gly Cys Thr Thr
               20             25

<210> SEQ ID NO 15
<211> LENGTH: 15
<212> TYPE: PRT
<213> ORGANISM: Artificial Sequence
<220> FEATURE:
<223> OTHER INFORMATION: Linker

<400> SEQUENCE: 15

Gly Gly Gly Gly Ser Gly Gly Gly Gly Ser Gly Gly Gly Gly Ser
1              5              10             15

<210> SEQ ID NO 16
<211> LENGTH: 5
<212> TYPE: PRT
<213> ORGANISM: Artificial Sequence
<220> FEATURE:
<223> OTHER INFORMATION: Linker

<400> SEQUENCE: 16

Gly Gly Gly Gly Ser
1              5

<210> SEQ ID NO 17
<211> LENGTH: 4
<212> TYPE: PRT
<213> ORGANISM: Artificial Sequence
<220> FEATURE:
<223> OTHER INFORMATION: Linker

<400> SEQUENCE: 17

Val Asp Gly Ser
1

<210> SEQ ID NO 18
<211> LENGTH: 4
<212> TYPE: PRT
<213> ORGANISM: Artificial Sequence
<220> FEATURE:
<223> OTHER INFORMATION: Linker

<400> SEQUENCE: 18

Ala Ser Gly Ser
1
```